US011020213B2

(12) United States Patent
Foote et al.

(10) Patent No.: US 11,020,213 B2
(45) Date of Patent: *Jun. 1, 2021

(54) FIXATION OF INTRALUMINAL DEVICE

(71) Applicant: BFKW, LLC, Grand Rapids, MI (US)

(72) Inventors: James A. Foote, Ada, MI (US); Frederick J. Walburn, Grand Rapids, MI (US); Randal S. Baker, Grand Rapids, MI (US)

(73) Assignee: BFKW, LLC, Ada, MI (US)

( * ) Notice: Subject to any disclaimer, the term of this patent is extended or adjusted under 35 U.S.C. 154(b) by 223 days.

This patent is subject to a terminal disclaimer.

(21) Appl. No.: 16/146,004

(22) Filed: Sep. 28, 2018

(65) Prior Publication Data

US 2019/0038394 A1 Feb. 7, 2019

Related U.S. Application Data

(63) Continuation-in-part of application No. 15/534,891, filed as application No. PCT/US2015/067407 on Dec. 22, 2015, now Pat. No. 10,682,219.
(Continued)

(51) Int. Cl.
A61F 2/04 (2013.01)
A61F 5/00 (2006.01)
A61B 17/064 (2006.01)

(52) U.S. Cl.
CPC .............. *A61F 2/04* (2013.01); *A61B 17/064* (2013.01); *A61F 5/0036* (2013.01);
(Continued)

(58) Field of Classification Search
CPC .............. A61F 2/848; A61F 2220/0016; A61F 2220/0008; A61F 2002/044; A61F 2002/045
See application file for complete search history.

(56) References Cited

U.S. PATENT DOCUMENTS 4,403,604 A 9/1983 Wilkinson et al.
4,607,618 A 8/1986 Angelchik
(Continued)

FOREIGN PATENT DOCUMENTS

EP 0760696 B1 8/2001
EP 1808888 A2 7/2007
(Continued)

OTHER PUBLICATIONS

International Search Report of the International Searching Authority from corresponding Patent Cooperation Treaty (PCT) Patent Application No. PCT/US12/38480, dated Jul. 30, 2012.
(Continued)

*Primary Examiner* — Diane D Yabut
(74) *Attorney, Agent, or Firm* — Gardner, Linn, Burkhart & Ondersma LLP

(57) ABSTRACT

An intraluminal device adapted to be positioned in a lumen that experiences peristalsis and method of fixation of an intraluminal device in the lumen, includes a wall configured to the size and shape of a portion of the lumen and at least one core. The at least one core is removably connected with a portion of the device wall. The at least one core is configured to be positioned against the lumen when the wall is positioned in the lumen. In this manner tissue envelopes the core during implantation of the intraluminal device. The at least one core is configured to be axially removable in situ from the tissue enveloping the core after the device has been deployed by disconnecting the core from the portion of the wall in order to explant the intraluminal device from lumen.

18 Claims, 25 Drawing Sheets

Related U.S. Application Data

(60) Provisional application No. 62/234,335, filed on Sep. 29, 2015, provisional application No. 62/151,150, filed on Apr. 22, 2015, provisional application No. 62/115,689, filed on Feb. 13, 2015, provisional application No. 62/097,295, filed on Dec. 29, 2014.

(52) U.S. Cl.
CPC .......... *A61F 5/0069* (2013.01); *A61F 5/0089* (2013.01); *A61B 2017/0641* (2013.01); *A61B 2017/0645* (2013.01); *A61F 2002/044* (2013.01); *A61F 2002/045* (2013.01); *A61F 2220/0016* (2013.01); *A61F 2220/0033* (2013.01); *A61F 2230/0093* (2013.01); *A61F 2250/006* (2013.01)

(56) References Cited

U.S. PATENT DOCUMENTS

| | | |
|---|---|---|
| 5,234,454 A | 8/1993 | Bangs |
| 5,306,300 A | 4/1994 | Berry |
| 5,366,504 A | 11/1994 | Andersen et al. |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A | 11/2000 | Andersen et al. |
| 6,264,700 B1 | 7/2001 | Kilcoyne et al. |
| 6,280,415 B1 | 8/2001 | Johnson |
| 6,312,437 B1 | 11/2001 | Kortenbach |
| 6,355,070 B1 | 3/2002 | Andersen et al. |
| 6,398,802 B1 | 6/2002 | Yee |
| 6,432,040 B1 | 8/2002 | Meah |
| 6,447,533 B1 | 9/2002 | Adams |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,800,081 B2 | 10/2004 | Parodi |
| 6,802,868 B2 | 10/2004 | Silverman et al. |
| 6,845,776 B2 | 1/2005 | Stack et al. |
| 6,916,332 B2 | 7/2005 | Adams |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,111,627 B2 | 9/2006 | Stack et al. |
| 7,146,984 B2 | 12/2006 | Stack et al. |
| 7,152,607 B2 | 12/2006 | Stack et al. |
| 7,211,114 B2 | 5/2007 | Bessler et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,449,024 B2 | 11/2008 | Stafford |
| 7,682,330 B2 | 3/2010 | Meade et al. |
| 7,704,264 B2 | 4/2010 | Ewers et al. |
| 7,708,752 B2 | 5/2010 | Durgin |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,815,591 B2 | 10/2010 | Levine et al. |
| 7,846,174 B2 | 12/2010 | Baker et al. |
| 7,922,650 B2 | 4/2011 | McWeeney et al. |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,162,871 B2 | 4/2012 | Levine et al. |
| 8,282,598 B2 | 10/2012 | Belhe et al. |
| 8,372,087 B2 | 2/2013 | Baker et al. |
| 8,447,403 B2 | 5/2013 | Sharma et al. |
| 8,506,477 B2 | 8/2013 | Waller et al. |
| 8,529,431 B2 | 9/2013 | Baker et al. |
| 8,672,831 B2 | 3/2014 | Baker et al. |
| 8,721,528 B2 | 5/2014 | Ho et al. |
| 8,778,011 B2 | 7/2014 | Ryan |
| 8,784,436 B2 | 7/2014 | Ho et al. |
| 8,801,599 B2 | 8/2014 | Baker et al. |
| 8,894,670 B2 | 11/2014 | Baker et al. |
| 9,055,998 B2 | 6/2015 | Baker |
| 9,198,789 B2 | 12/2015 | Baker et al. |
| 9,375,338 B2 | 6/2016 | Baker et al. |
| 9,414,948 B2 | 8/2016 | Baker et al. |
| 9,545,326 B2 | 1/2017 | Baker et al. |
| 9,839,545 B2 | 12/2017 | Baker et al. |
| 9,872,787 B2 | 1/2018 | Baker et al. |
| 10,182,901 B2 | 1/2019 | Baker et al. |
| 2001/0020189 A1 | 9/2001 | Taylor |
| 2002/0032487 A1 | 3/2002 | Dua et al. |
| 2002/0091395 A1 | 7/2002 | Gabbay |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0109935 A1 | 6/2003 | Geitz |
| 2003/0199989 A1 | 10/2003 | Stack et al. |
| 2003/0212450 A1 | 11/2003 | Schlick |
| 2004/0044357 A1 | 3/2004 | Gannoe et al. |
| 2004/0087976 A1 | 5/2004 | DeVries et al. |
| 2004/0092892 A1 | 5/2004 | Kagan et al. |
| 2004/0106987 A1 | 6/2004 | Palasis et al. |
| 2004/0116999 A1 | 6/2004 | Ledergerber |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0172141 A1 | 9/2004 | Stack et al. |
| 2004/0210111 A1 | 10/2004 | Okada |
| 2004/0220682 A1 | 11/2004 | Levine et al. |
| 2005/0004582 A1 | 1/2005 | Edoga et al. |
| 2005/0043683 A1 | 2/2005 | Ravo |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251165 A1 | 11/2005 | Vaughan et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |

(56) References Cited

U.S. PATENT DOCUMENTS

| | | |
|---|---|---|
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208429 A1 | 9/2007 | Leahy |
| 2007/0233221 A1 | 10/2007 | Raju |
| 2007/0260112 A1 | 11/2007 | Rahmani |
| 2007/0276432 A1 | 11/2007 | Stack et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1* | 2/2010 | Baker .................. A61F 2/04 600/37 |
| 2010/0114124 A1 | 5/2010 | Kelleher et al. |
| 2010/0114130 A1 | 5/2010 | Meade et al. |
| 2010/0256775 A1 | 10/2010 | Belhe et al. |
| 2010/0280313 A1 | 11/2010 | Gasche et al. |
| 2011/0004146 A1 | 1/2011 | Priplata et al. |
| 2011/0009690 A1 | 1/2011 | Belhe et al. |
| 2011/0264234 A1 | 10/2011 | Baker et al. |
| 2012/0083871 A1 | 4/2012 | Ryan |
| 2012/0095497 A1 | 4/2012 | Babkes et al. |
| 2012/0191213 A1 | 7/2012 | Baker et al. |
| 2012/0191215 A1 | 7/2012 | Baker et al. |
| 2012/0203061 A1 | 8/2012 | Birk |
| 2013/0123811 A1 | 5/2013 | Baker et al. |
| 2013/0296913 A1 | 11/2013 | Foote et al. |
| 2013/0324902 A1 | 12/2013 | Miller et al. |
| 2015/0039092 A1 | 2/2015 | Baker et al. |
| 2015/0182239 A1 | 7/2015 | Baker et al. |
| 2016/0151233 A1 | 6/2016 | Baker et al. |
| 2017/0172723 A1 | 6/2017 | Foote et al. |

FOREIGN PATENT DOCUMENTS

| | | |
|---|---|---|
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | WO 2010/117641 A2 | 10/2010 |
| WO | WO 2011/056608 A1 | 5/2011 |
| WO | WO 2011/063307 A1 | 5/2011 |
| WO | WO 2011/097209 A1 | 8/2011 |
| WO | WO 2011/116025 A1 | 9/2011 |
| WO | WO 2012/044917 A1 | 4/2012 |
| WO | WO 2012/136249 A1 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2015/031077 A1 | 3/2015 |
| WO | WO 2016/109346 A1 | 7/2016 |

OTHER PUBLICATIONS

International Preliminary Report on Patentability and Written Opinion of the International Searching Authority from corresponding Patent Cooperation Treaty (PCT) Patent Application No. PCT/US12/38480, dated Nov. 29, 2013.

"Obesity: Super-Sized Medical Device Market", Start-Up, Mar. 2003, Technology Strategies (Long Article), pp. 1-10 and a cover page.

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Esophageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Pat. No. 6,960,233 annotated by the Israel Patent Office (Nov. 1, 2005).

Schembre, Drew, "Advances in Esophageal Stenting: the Evolution of Fully Covered Stents for Malignant and Benign Disease," Adv. Ther., Springer Healthcare, Apr. 1, 2010, pp. 1-13.

International Preliminary Report on Patentability and Written Opinion of the International Searching Authority from corresponding Patent Cooperation Treaty (PCT) Patent Application No. PCT/US08/53912, dated Aug. 19, 2009.

International Preliminary Report on Patentability and Written Opinion of the International Searching Authority from corresponding Patent Cooperation Treaty (PCT) Patent Application No. PCT/US05/36991, dated Mar. 6, 2006.

S. Fukudo, T. Nomura, M. Hongo, "Impact of corticotropin-releasing hormone on gastrointestinal motility and adrenocorticotropic hormone in normal controls and patients with irritable bowel syndrome", Jan. 19, 1998.

D.G. Maxton, D.F. Martin, P.J. Whorwell, M. Godfrey. "Abdominal distension in female patients with irritable bowel syndrome: exploration of possible mechanisms", Aug. 3, 1990.

* cited by examiner

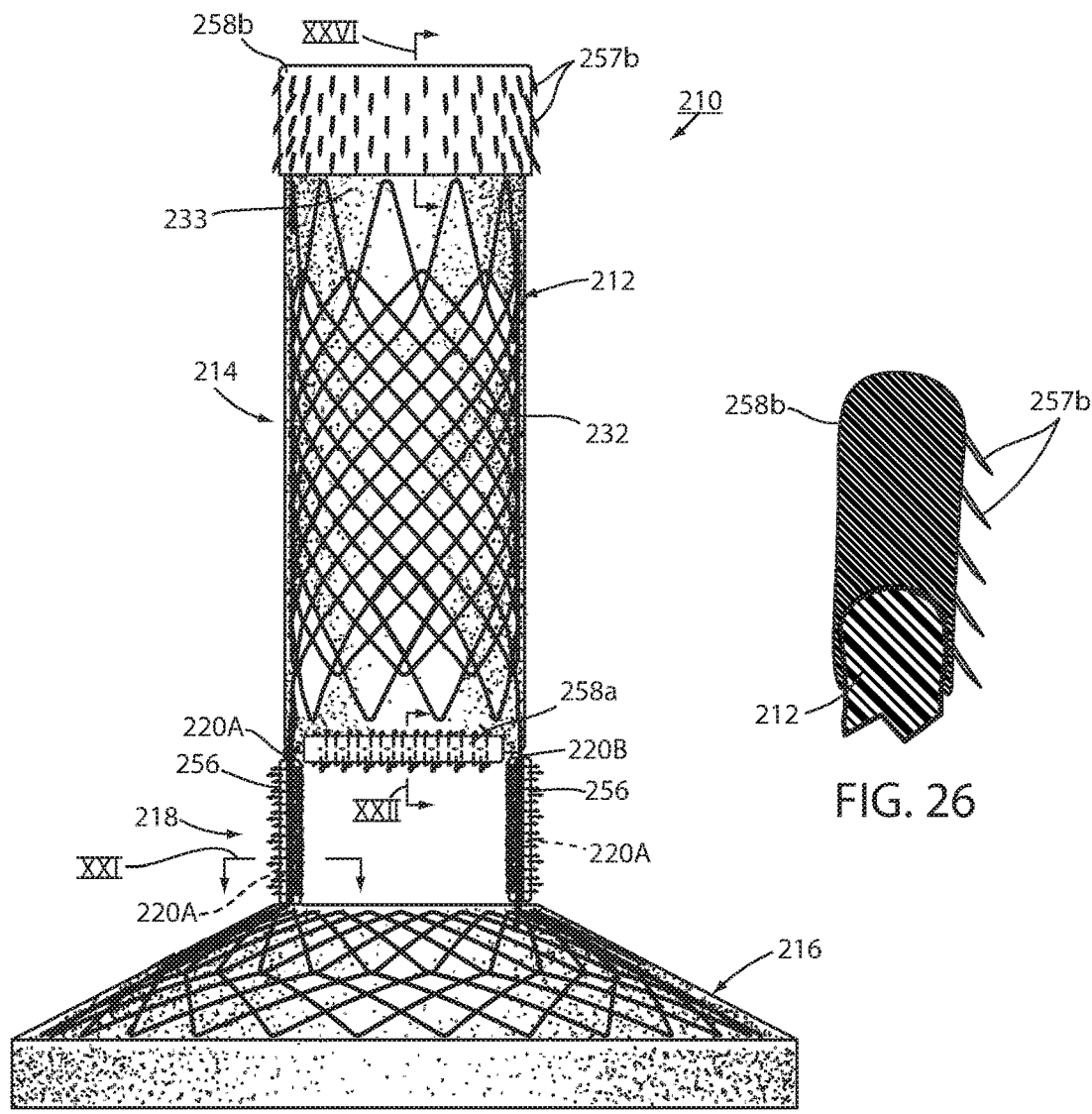
FIG. 19
FIG. 26
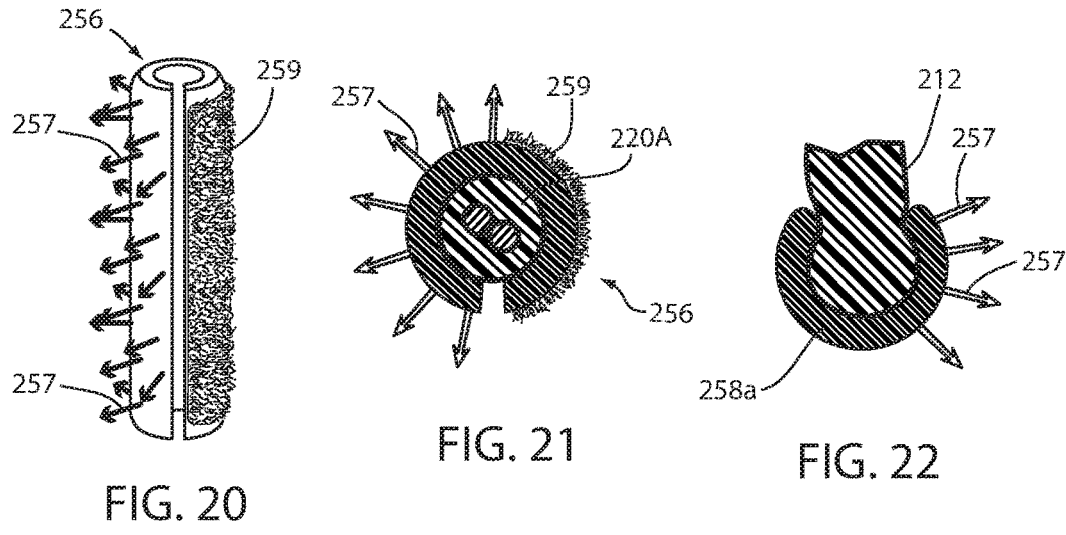
FIG. 20
FIG. 21
FIG. 22

FIXATION OF INTRALUMINAL DEVICE

CROSS REFERENCE TO RELATED APPLICATIONS

The present application is a continuation-in-part of U.S. patent application Ser. No. 15/534,891, filed Jun. 9, 2017, which claims the priority benefits of International Patent Application No. PCT/US2015/067407, filed Dec. 22, 2015, which claims priority from U.S. patent application Ser. No. 62/234,335, filed on Sep. 29, 2015, and U.S. patent application Ser. No. 62/151,150, filed on Apr. 22, 2015, and U.S. patent application Ser. No. 62/115,689, filed on Feb. 13, 2015, and U.S. patent application Ser. No. 62/097,295, filed on Dec. 29, 2014, which are all hereby incorporated by reference herein in their entireties.

BACKGROUND OF THE INVENTION

The present invention is directed to an intraluminal device and method of fixation of an intraluminal device and, in particular, a technique that enhances both fixation and removability of the device. While the invention is illustrated for use with a bariatric device and/or a metabolic device, it may be applied to other intraluminal devices positioned in a mammalian lumen or hollow organ that is subject to peristalsis, such as an esophageal stent, an anti-reflux device, a nasal gastric tube, an intestinal sleeve, and the like, including devices positioned in the fallopian tubes, vas deferens, and the like.

SUMMARY OF THE INVENTION

An intraluminal device and method of providing satiety and/or treating a metabolic disease in a recipient is disclosed in U.S. Pat. Nos. 7,846,174; 8,100,931; 8,372,087; 8,529,431; 8,672,831; 8,801,599 and 8,894,670 and published PCT Application No. WO2015/031077 A1, the disclosures of which are hereby incorporated herein by reference in their entirety. Such devices and methods apply stress to the gastro-intestinal tract in general and in particular to the cardiac portion of the stomach of the recipient to produce satiety in the absence of food to produce satiety, and to augment fullness caused by food, and/or to treat a metabolic disease. A challenge with such devices and methods is fixation of a portion of the device against a surface of the GI tract, such as the cardiac portion of the stomach in the presence of peristalsis tending to cause distal migration of the device.

While the use of tissue ingrowth patented in the above-identified patents has been found to provide a satisfactory solution for fixation to resist distal migration, aspects of the present invention includes providing short-term fixation of the device until the tissue ingrowth providing long-term fixation is in place. Such short-term fixation is easy to carry out and capable of complete fixation over the days or weeks that it takes for the long-term fixation to occur.

Aspects of the present invention provide techniques for explantation of an intraluminal device having a wall that is configured to be positioned in a lumen. At least one core is removably connected with a portion of the wall and is positioned against lumen tissue when the wall is positioned in the lumen such that tissue envelopes of or encases the core during deployment or implantation of the device. Explantation of the device should not substantially damage the lumen of the recipient or require that the lumen be incised in order to separate the core from the lumen. Aspects of the present invention facilitate such explantation and provide techniques that may beneficially utilize such tissue encasing the connector for immediate and/or long-term fixation of an intraluminal device against distal migration caused by peristalsis.

An intraluminal device adapted to be positioned in a lumen that experiences peristalsis, according to an aspect of the invention, includes a wall configured to the size and shape of a portion of the lumen and at least one core. The at least one core is removably connected with a portion of the wall and adapted to be disconnected in situ from the portion of the wall. The at least one core is configured to be positioned against the lumen when the wall is positioned in the lumen. In this matter tissue envelopes the core during implantation of the device. The at least one core is configured to be axially removable from the tissue enveloping the core when the at least one core is disconnected from the portion of the wall in order to explant the intraluminal device from the lumen.

The at least one core may be removably connected with the portion of the wall by being configured to be axially movable with respect of another portion of the wall. The at least one core may include at least two cores that are each removably connected with a different portion of the wall by being configured to be axially movable with respect to other portions of said wall.

The at least one core may include at least two cores that are each removably connected with a different portion of the wall. The wall may be made of at least two separate wall portions that are connected together with the at least one core and the at least one core be removably connected with at least one of said at least two wall portions. The at least one core may be axially removable from the lumen in order to explant the intraluminal device from the lumen tissue enveloping the core when the core is disconnected from said at least one of the at least two wall portions. In this aspect of the invention, the at least one core may be referred to a connector, a strut, or a tension member because the at least one core applied force between the at least two wall portions which would separate in use if not for the at least one core.

A fastener may be provided that is adapted to fasten the at least one core to the lumen in order to fix the intraluminal device in the lumen. The fastener may be a suture. The fastener comprises a clip. The fastener may be adapted to be applied intraluminally. The fastener may be at an upstream end portion of the at least one core.

The at least one core may be removably connected with the portion of the wall with a removable attachment and wherein the at least one core is separable by removing the removable attachment. The removable attachment may be a severable filament. An enlarged member may be on the at least one core to space said severable filament from the wall for access to the filament. The at least one core may be coated with a bio-compatible material that extends around the at least one core.

The wall may be formed as an esophageal stent, an anti-reflux device, a nasal gastric tube, an intestinal sleeve, a bariatric device, or a metabolic disease treatment device.

A method of fixation of an intraluminal device in a lumen that experiences peristalsis, according to an aspect of the invention, includes the intraluminal device having a wall configured to the size and shape of a portion of the lumen and at least one core. The at least one core is removably connected with a portion of the wall and adapted to be disconnected in situ from the portion of the wall. The at least one core is positioned against the lumen when the wall is positioned in the lumen. In this manner, tissue envelopes the core during implantation of the device in the lumen. The at least one core is disconnected from the portion of the wall and the at least one core axially removed from the tissue enveloping the at least one core in order to explant the intraluminal device from the lumen.

The at least one core is disconnected from the portion of the wall by axially moving the at least one core with respect to said another portion of said wall. The at least one core may include at least two cores that are each removably connected with a different portion of the wall. The at least two cores may be disconnected by axially moving the at least two cores with respect to other portions of the wall.

The at least one core may be at least two cores that are each removably connected with a different portion of the wall. The wall made be made up of two or more separate wall portions that are connected together with the core. The core may be removably connected with at least one of said at least two wall portions and axially removed from the lumen in order to explant the intraluminal device from the lumen tissue enveloping the core. This includes disconnecting the cores from said least one of said at least two wall portions and separately removing the at least two separate wall portions from the lumen.

The core may be fastened to the lumen with a fastener in order to fix the intraluminal device in the lumen. The fastener may be a suture and the fastening includes applying the suture to the to the lumen. The suture may be applied around the core when applied to the lumen and a portion of lumen tissue wrapped around the core when applying the suture around the core. The fastener may be a clip. The fastener may be applied intraluminally. The fastener may be applied at an upstream end portion of said core.

The at least one core may be removably connected with the portion of the wall with a removable attachment and may be separated from the wall by removing said removable attachment. The removable attachment may be a severable filament. An enlarged member may be provided on the severable filament to space the severable filament from the wall for access to the filament.

The at least one core may be coated with a bio-compatible material that extends around the at least one core. The intraluminal device may be used as an esophageal stent, an anti-reflux device, a nasal gastric tube, an intestinal sleeve, a bariatric device, or a metabolic disease treatment device. The tissue of the lumen where the core is positioned against the lumen may be disrupted to promote the tissue enveloping the core. Such disrupting of the tissue may be using cauterization, ultrasound therapy, and/or cryro-therapy.

These and other objects, advantages, purposes and features of the present invention will become apparent upon review of the following specification in conjunction with the drawings.

BRIEF DESCRIPTION OF THE DRAWINGS

FIG. 19 is a side elevation of an alternative embodiment of a bariatric device;

FIG. 20 is a perspective view of a retainer that is capable of short-term fixation and facilitating long-term fixation;

FIG. 21 is a sectional view taken along the lines XXI-XXI in FIG. 19;

FIG. 22 is a sectional view taken along the lines XXII-XXII in FIG. 19;

FIG. 26 is a sectional view taken along the lines XXVI-XXVI in FIG. 19;

DESCRIPTION OF THE PREFERRED EMBODIMENTS

Figure 1:
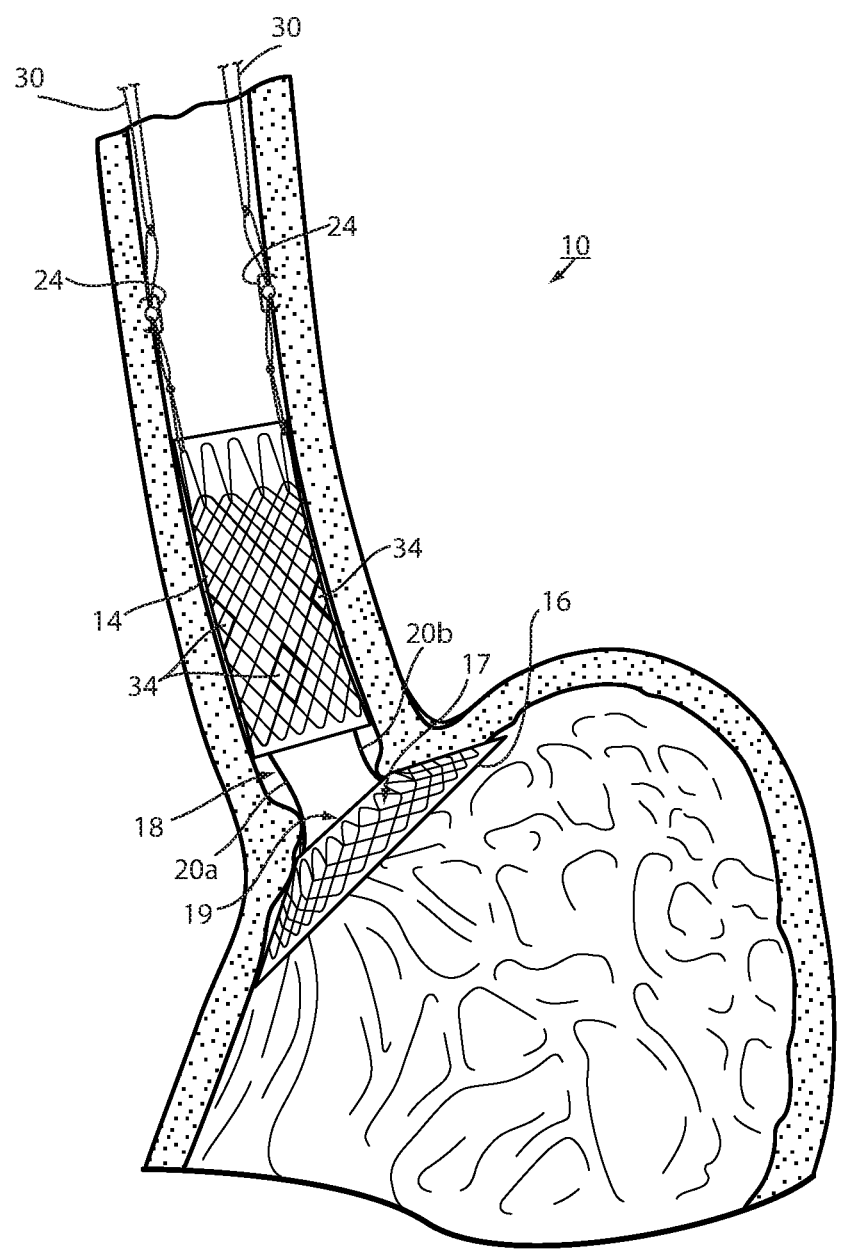
FIG. 1 is a cross section of an intraluminal device deployed in a mammalian lumen or hollow organ of a recipient, namely, a bariatric device at the gastroesophageal (GE) region of the recipient.

Referring now to the drawings and the illustrative embodiment depicted therein, an intraluminal device, such as a bariatric device or a metabolic disease treatment 10, has a wall 12 defining an esophageal portion 14 that is configured to the size and shape of a portion of a mammalian lumen or hollow organ, namely, the esophagus, a cardiac portion 16 that is configured to the size and shape of a separated portion of mammalian lumen or hollow organ, namely, the cardiac portion of the stomach and a connector 18 connecting esophageal portion 14 and cardiac portion 16 (FIGS. 1-5). While illustrated as a bariatric device, it should be understood that that principles of the invention are applicable to other intraluminal devices that are positioned in a lumen or hollow organ that experiences peristalsis, such as an esophageal stent, an anti-reflux device, a nasal gastric tube, an intestinal sleeve, and the like. Also, the invention may be applied to a metabolic disease treatment device and method as disclosed in commonly assigned International Patent Application Publication No. WO2015/031077 A1, the disclosure of which is hereby incorporated by reference in its entirety.

Figure 2:
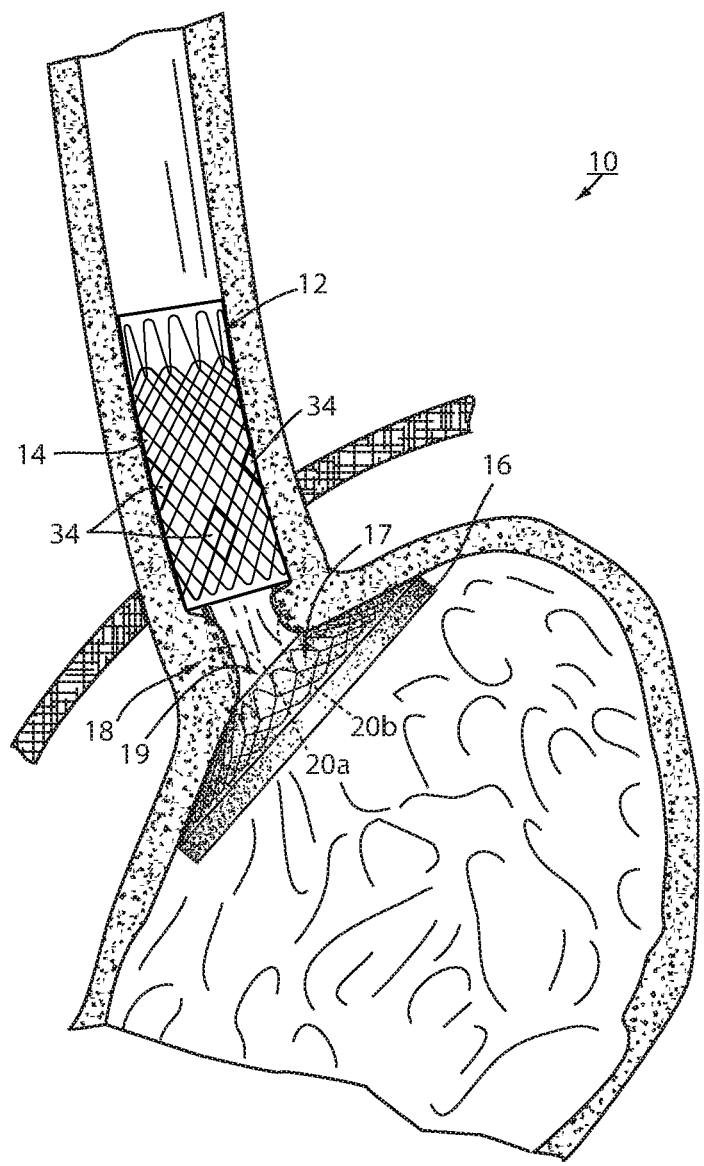
FIG. 2 is the same view as FIG. 1 after the device has been deployed at the GE region for a period of time, such as several weeks or months.

As can be seen in FIGS. 1 and 2, intraluminal device 10 is positioned at the gastroesophageal region with the esophageal portion 14 in the esophagus, the cardiac portion 16 at the cardiac portion of the stomach and at least a portion of connector 18 extending through the gastroesophageal (GE) junction. In the illustrated embodiment, connector 18 is made up of two elongated filaments 20a, 20b which are in tension and may be referred to as struts. As can be seen by comparing FIGS. 1 and 2, with device 10 fixed at the gastroesophageal region to cause body mass loss, mucosa (which may include submucosa and even muscular) tissue bridges over at least one of the two struts 20a, 20b as shown in FIG. 2 after device 10 has been positioned in the GE region. The bridging tissue can fuse with time sufficiently to achieve significant loss of excess body mass making it difficult to explant intraluminal device 10. Also, as will be discussed in more detail below, tissue bridging of struts 20a, 20b may provide long-term fixation of device 10, alone or in combination with other functions in accordance with the principles set forth in commonly assigned U.S. Pat. No. 8,894,670 B2. In particular, the struts correspond to the bridge in the '670 patent and the spaces between the struts correspond to the openings adjacent the bridge in the '670 patent so that the tissue bridging over the struts implements mucosal capture patented in the '670 patent.

Fixation of intraluminal device 10 against distal migration includes a fixation technique 22 that fastens esophageal portion 14 with the esophagus with a fastener such as a tissue penetrating fastener 24. A looped filament 26 extending proximally from esophageal portion 14 is captured with fastener 24 engaging the wall of the esophagus by the fastener. The loops in the looped filament are positively engaged by the fastener so that the esophageal portion 14 is firmly fixed to the esophagus by the fastener. The number of loops can vary from one to many and can be any size or shape as long as they are a closed polygon. In the illustrated embodiment, fastener 24 is an endoscopically deployed clip marketed by Ovesco and described in detail in U.S. Pat. No. 8,721,528 for an ENDOSCOPE CAP, the disclosure of which is hereby incorporated herein by reference. Also, although two loops and penetrating fasteners are illustrated, one or more than two may be used.

Figure 4:
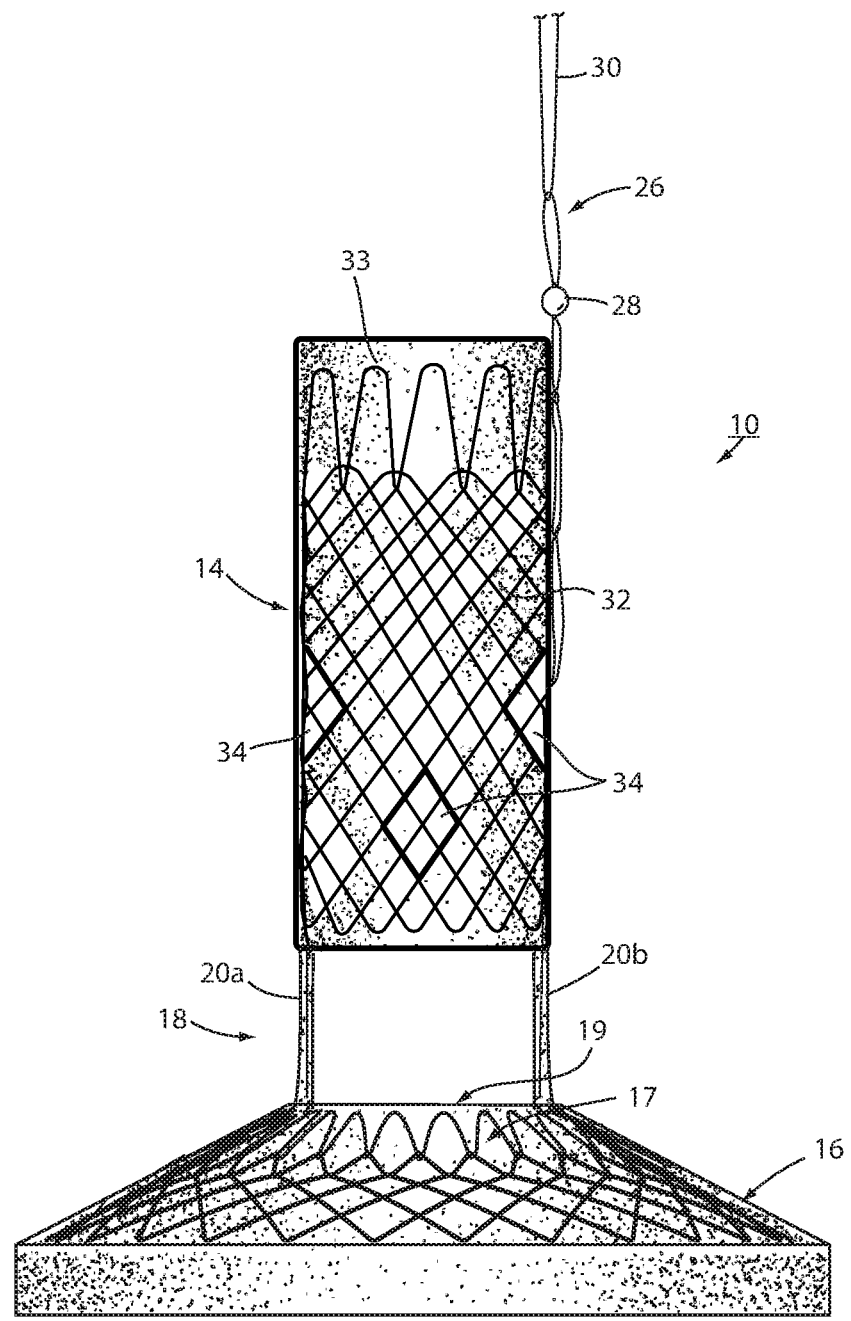
FIG. 4 is the same view as FIG. 3 of an alternative embodiment thereof.

Fixation technique 22 is intended to provide at least temporary fixation to maintain device 10 in position at the GE region of the recipient with cardiac portion 16 engaging the cardiac region of the stomach while permanent fixation develops. Looped filament 26 may be at least partially elastic in order to be slightly stretched when fastener 24 is deployed to maintain upward pressure on cardiac portion 16 after deployment. Looped filament 26 may be at least partially bioabsorbable, or resorbable, so that it, along with fastener 24, may fall away after permanent fixation occurs as seen in FIG. 2. Looped filament 26 may be made from monofilament or braided filament. An enlarged portion 28 of filament 26 may be provided and fastener 24 applied at or adjacent tissue of the esophageal wall that is drawn over the enlarged portion 28 by suction. Alternatively, the fastener 24 may be applied adjacent the enlarged portion 28, such as distal the enlarged portion. The enlarged portion and the loops defining looped filament 26 provide engagement between the mechanical fastener and the looped filament to prevent the looped filament from pulling away from the fastener. In the illustrated embodiment, enlarged portion 28 is a bead. As illustrated in FIG. 4, it may be desirable to position enlarged portion 28 as close as possible to esophageal member 14 to avoid entanglement between a retainer filament 30 discussed below and another retainer filament (not shown) that extends proximally from esophageal member 14.

A retainer filament 30 may be temporarily connected with the looped filament 26 and extending external the recipient of the device from the esophagus. Retainer filament 30 allows the physician or other healthcare worker the ability to position bariatric device 10 properly at the GE region and to apply tension to looped filament 26 until fastener 24 is applied. As retainer filament 30 is merely looped proximally to looped filament 26, it can be easily retraced by pulling on one side of the loop. Looped filament 26 is connected directly with the mesh 32 that provides a structure to bariatric device 10. This allows the looped filament to apply proximal axial force to mesh which force is then distributed over wall 12 without causing a narrowing of esophageal portion 14 as may occur if the looped filament were to be connected with a removal suture (not shown) that encircles esophageal portion 14 proximally and is used to remove device 10. If a proximal force were to be applied to such removal suture, the diameter of esophageal portion 14 may be reduced upon fixation thus counteracting mucosal capture and/or tissue ingrowth of the wall of the esophageal portion to the esophageal wall. While the application of proximal axial force to such removal suture, or ring, may be a useful action to explant intraluminal device 10, it would not be useful in providing fixation.

Figure 3:
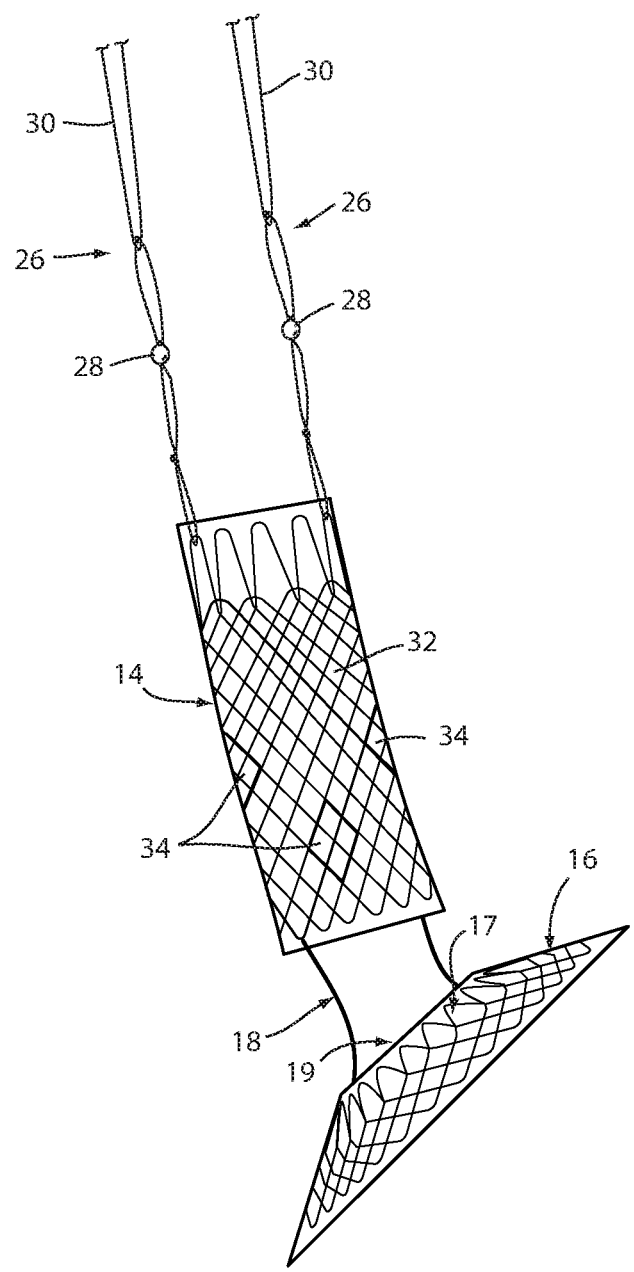
FIG. 3 is a side elevation of the device in FIGS. 1 and 2.

Thus, the direct connection of looped filament 26 to mesh 32 allows proximal axial force to be applied to esophageal portion 14 without inducing a radially inward force tending to pull wall 12 away from the esophagus wall. While looped filament 26 is shown in FIG. 1 and FIG. 3 connected with a proximal end portion of mesh 32, it could also be connected at a central or distal portion of the mesh as shown in FIG. 4. While filament 26 could extend from the interior of esophageal portion 14, it could also extend from an outer surface of the esophageal member wall, as shown in FIG. 4, thereby ensuring that any tension force on filament 26 tends to pull the esophageal member wall toward the esophagus wall. Also, as shown in FIG. 4, cardiac portion 16 may include a transition zone 17 adjacent its proximal opening 19 in order to resist any irritation of the tissue of the cardiac portion of the stomach in accordance with the principles set forth in commonly assigned International Patent Application Publication No. WO2012/044917, the disclosure of which is hereby incorporated herein by reference in its entirety.

Figure 6:
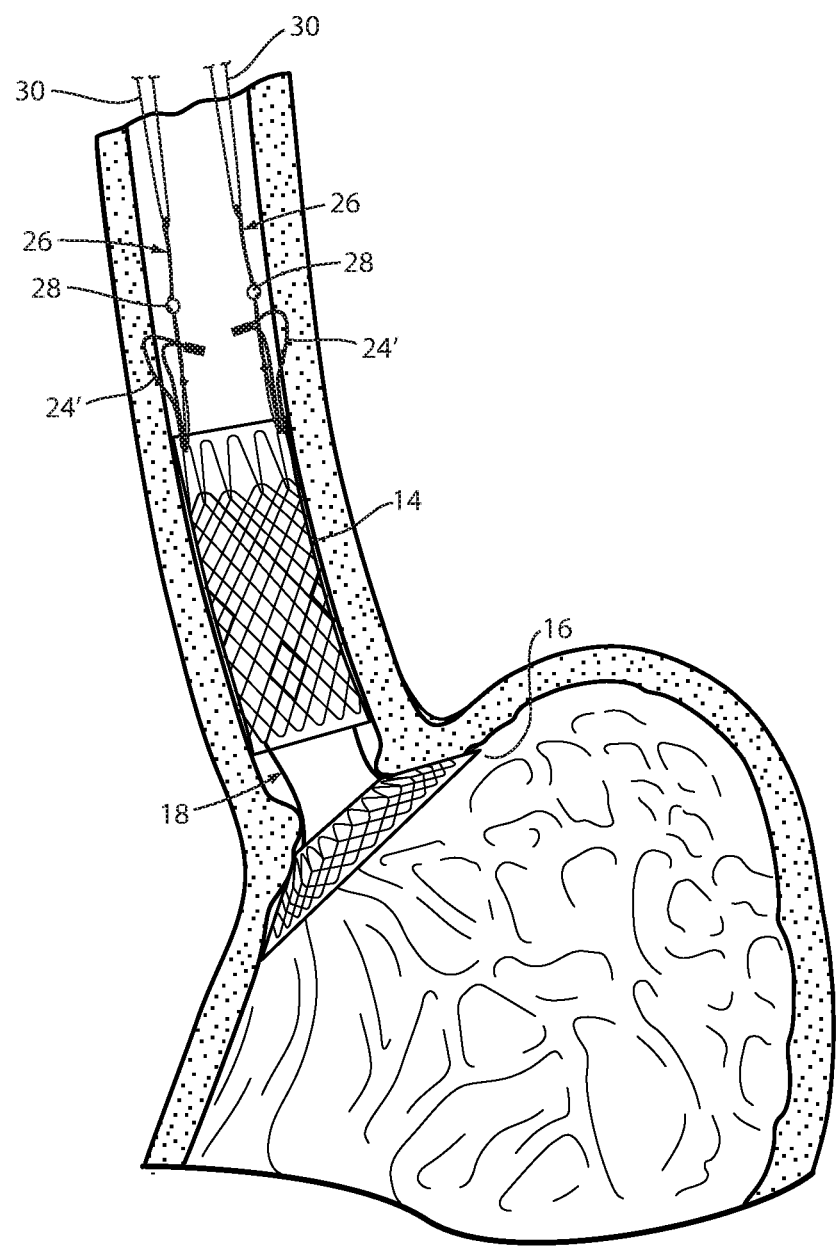
FIG. 6 is the same view as FIG. 1 showing an alternative short-term fixation of the device.

In an alternative technique illustrated in FIG. 6 temporary fixation is provided by a tissue penetrating fastener in the form of sutures 24'. Each suture 24' is passed through the wall of esophageal portion 14 and at least partially through the wall of the esophagus of the recipient. The suture may be applied endoscopically, such as by using an automated suture device that is commercially available such as one marketed by Apollo Endosurgery. The suture is preferably made from an absorbable material so that it dissolves over time as more permanent fixation from tissue capture takes over. In the embodiment used in FIG. 6, looped filament 26 is used to transmit the retaining force from retainer filament 30 to the esophageal member 14 but does not form a part of temporary fixation. It would be possible to attach retainer filament 30 directly to esophageal portion 14.

Fixation of device 10 against distal migration includes temporary fixing, such as using fixation 22, and long-term fixing from wall characteristics that fixes the wall to the GE region through growth of tissue, such as using tissue ingrowth zones 34 formed in wall 12.

Figure 5:
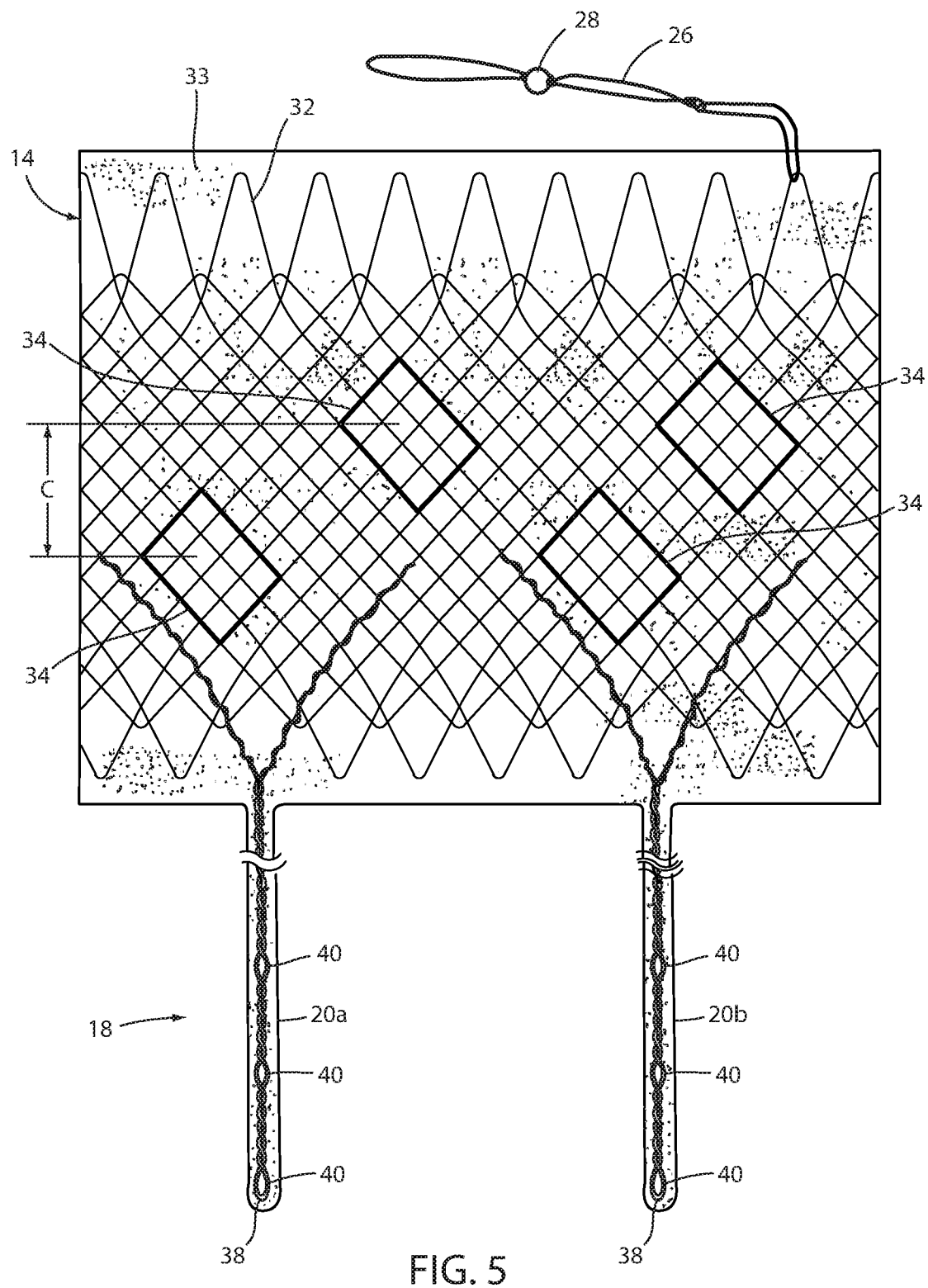
FIG. 5 is a plan view of the esophageal portion and connector portions of FIG. 3 with the esophageal portion unrolled into a flat state.

Tissue ingrowth zones 34 are openings in the cover 33 of biocompatible material, such as silicone, over mesh 32, which openings allow tissue to grow over members of the mesh. As shown in FIG. 5 and as disclosed in U.S. Pat. Application Publication No. 2014/0121585 entitled INTRALUMINAL DEVICE AND METHOD WITH ENHANCED ANTI-MIGRATION, the disclosure of which is hereby incorporated herein by reference, zones 34 are more effective if spaced apart a distance "C" in the direction of peristalsis on an order of magnitude of at least the wavelength of the peristaltic wave. Long-term fixation using ingrowth openings 34 may be removed to explant device 10, such as by cauterizing the tissue in the mucosal capture zones 34 and by placing an inward radial force on esophageal portion 14 such as by applying a proximal force on the removal suture (not shown) in order to remove device 10. Also, an over tube, of the type known in the art, may be inserted between esophageal portion 14 and the wall of the esophagus to further separate wall 12 from the tissue of the esophagus. Other techniques for removing mucosa from openings 34, such as mechanical severing of the tissue, will be apparent to the skilled artisan.

Tissue at or adjacent the GE junction, which includes tissue immediately above and below the sphincter, may bridge over one or both struts 20a, 20b of connector portion 18 at the GE junction as seen in FIG. 2 after bariatric device 10 has been deployed for several weeks or months. Such tissue bridging over struts 20a, 20b may be difficult to remove, such as by merely placing a radial inward force on the struts. It will be appreciated that struts 20a, 20b could not be readily axially displaced with esophageal portion 14 close to the GE junction and cardiac portion 16 against the stomach wall because esophageal portion 14 and cardiac portion 16 are much larger than either strut 20a, 20b and, therefore, could not be pulled through the opening in the bridging tissue. In order to remove struts 20a, 20b to explant device 10, struts 20a, 20b of connector portion 16 of wall 12 are axially displaced, or pulled, from the gastroesophageal junction to remove the connector from the bridging tissue to remove the bariatric device.

Figure 7:
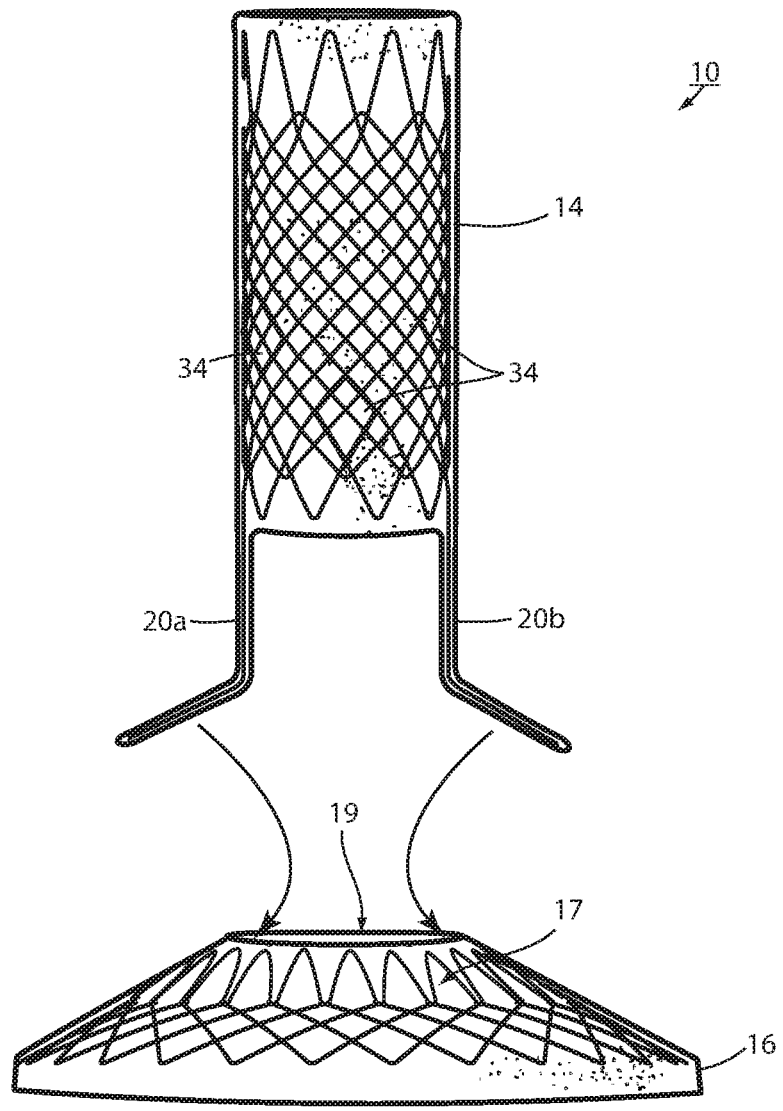
FIG. 7 is a side elevation of a bariatric device showing the principle of removable attachment between the connector portion and the cardiac portion.
Figure 7A:
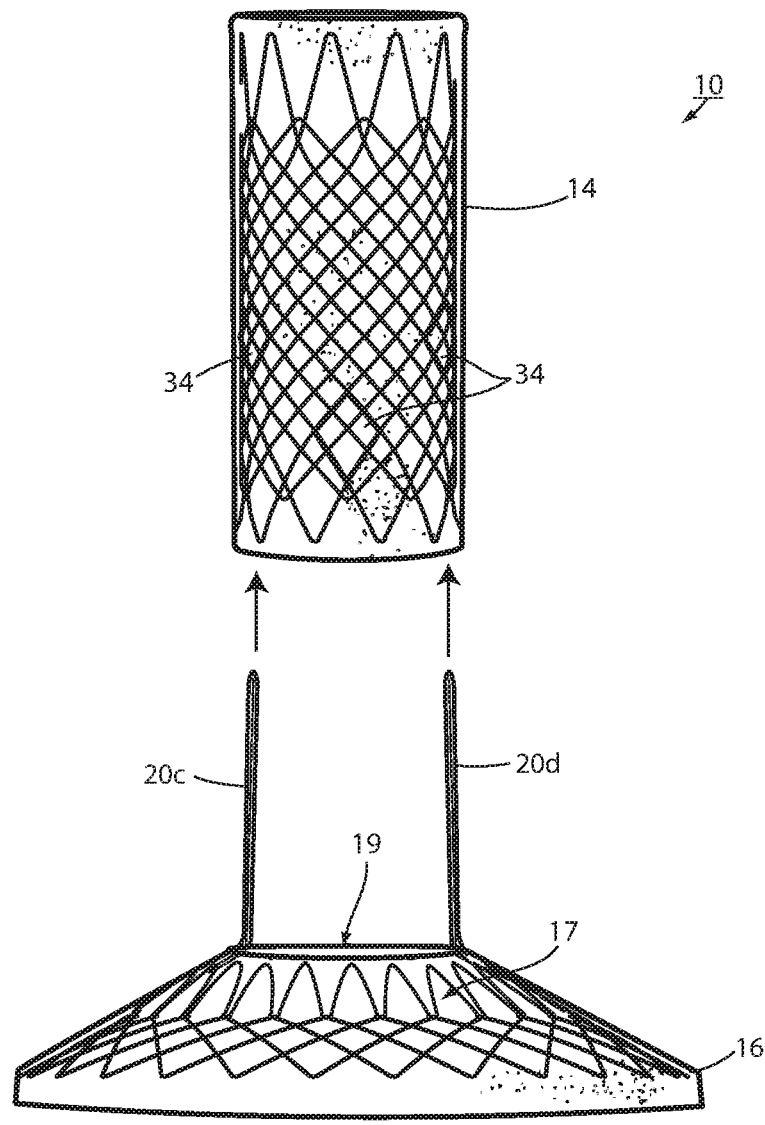
FIG. 7A is the same view as FIG. 7 illustrating an alternative embodiment thereof.

This could at least theoretically be achieved by physically severing the struts, such as using an argon beam coagulator, or the like. In the illustrated embodiments, such axial displacement of the struts is achieved by making struts 20a and 20b separable from the portion of the device wall 12 defining cardiac portion 16 and by separating the struts from the device wall as seen in FIG. 7 or by making struts 20c and 20d separable from the portion of the device wall defining esophageal portion 14 and separating the struts from the device wall as seen in FIG. 7A. Struts 20a, 20b, 20c, 20d are adapted to be separated by being removably attached with a removable attachment 42 to wall 12. The struts can be separated by removing the removable attachment.

Once free of the cardiac portion 16, struts 20a, 20b may be axial withdrawn, or pulled, proximally through the bridging tissue of the GE junction by axial proximal displacement of esophageal portion 14 in the manner discussed above. Once the struts are withdrawn, the esophageal portion 14 can be retracted proximal, using a removal suture (not shown), or the like. The cardiac portion 16 can be removed from the stomach by drawing it into an over tube inserted in the esophagus or other such method. Once free of esophageal portion 14, struts 20c, 20d may be withdrawn, or pulled, proximally through the bridging tissue of the GE junction by axially distal displacement of cardiac portion 16 into the stomach where it can be removed as discussed above. The esophageal portion 14 can be withdrawn proximally. While the embodiment disclosed in FIG. 7A requires that a force be applied to the cardiac portion 16 to axially separate the struts 20c, 20d from the bridging tissue, an advantage of this embodiment is that the removable attachment 42 is located at the esophageal portion 14 where it is more easily accessed in order to remove the attachment.

Struts 20a, 20b, 20c, 20d may be each formed from a single continuous metallic filament 38, such as Nitinol or stainless steel that is twisted from distally to proximally as shown in FIG. 4. As filament 38 is wound, several openings 40 may be formed in struts 20a, 20b, 20c, and 20d as will be described below. Ends of filament 38 may be woven with the mesh 32 of esophageal portion 14 or of the mesh of the cardiac portion 16 or otherwise attached as seen in FIG. 5. Struts 20a, 20b, 20c, 20d are coated with silicone or other biocompatible material to ease axial withdrawal from the tissue bridging the struts. Also, struts 20a, 20b, 20c, 20d may have an optional elastic portion (not shown) to enhance proximal force placed on cardiac portion 16 to ensure satiety. Also, struts 20a, 20b, 20c, 20d may include a therapeutic agent eluting coating that applies a therapeutic agent, such as an anesthesia, or the like. This coating may elute the agent for a limited period, such as two weeks, after deployment, to ensure pain-free embedding of the struts in the recipient. Alternatively, an agent-dispensing reservoir could be at a distal portion of esophageal portion 14 to dispense a controlled amount of a therapeutic agent, such as an anesthesia to the tissue engaging the struts. In addition to the struts, a therapeutic agent eluting coating may be applied to the area surrounding tissue ingrowth zones 34 and perhaps other areas of device 10. For example, a different type of agent, such as to encourage tissue fibrosis and ingrowth, may be eluted to encourage earlier and stronger long-term fixation.

Figure 8:
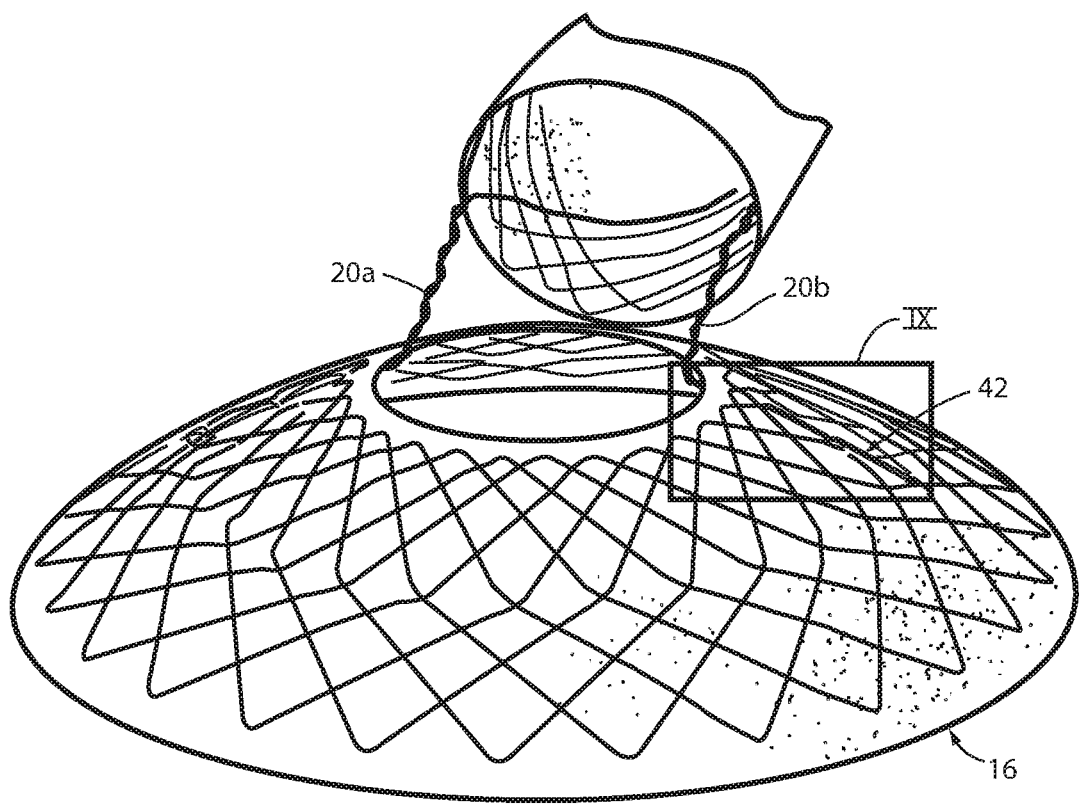
FIG. 8 is a perspective view of the device in FIG. 7 taken from the side and proximal, or top direction illustrating details of the removable attachment.
Figure 9:
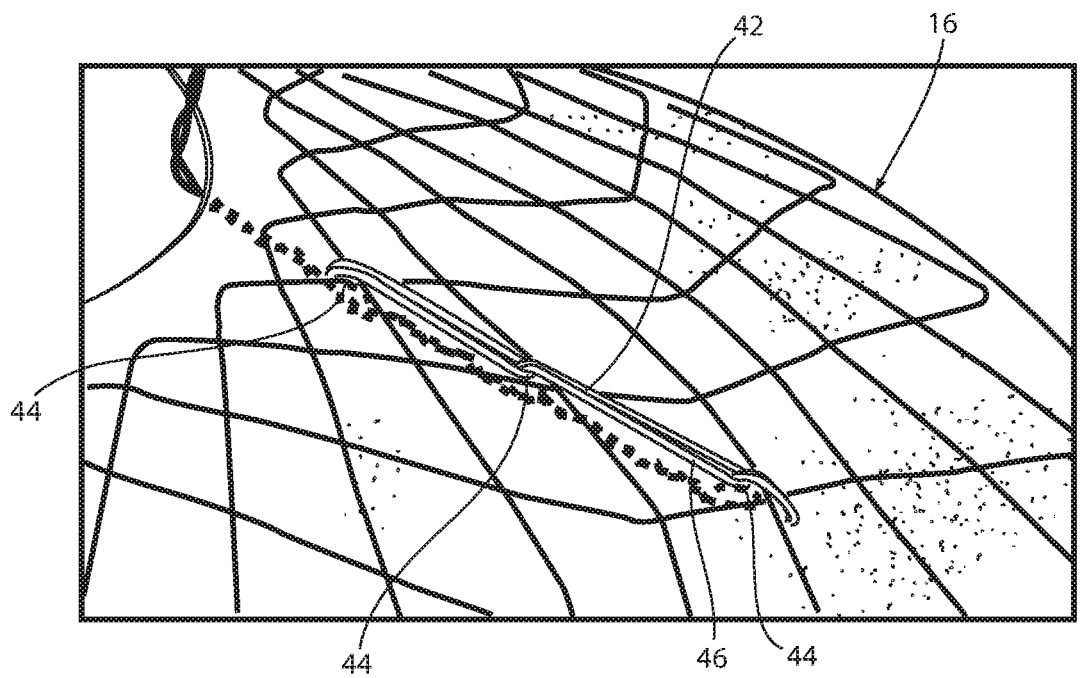
FIG. 9 is an enlarged perspective view of the portion shown at IX in FIG. 8.

In one embodiment, removable attachment 42 includes a separable portion of struts 20a, 20b, 20c, 20d extending along the surface of wall 12 as seen in FIGS. 8 and 9.

Openings 40 are arranged to register with intersections 44 in the portion of mesh 32 of wall 12. Removable attachment 42 is illustrated as a chain stitch 46 between one or more openings 40 and corresponding intersections 44. The stich is made with a filament, such as high-strength suture material, or the like. The advantage of a chain stitch, which is known in the art, is that it can be completely removed by severing its filament, such as with an endoscopic scissors or heating device, at any place such along the filament. Once removable attachment 42 is severed at separable portions of both struts 20a, 20b, esophageal portion 14 can be proximally withdrawn thus axially liberating the struts from the captured tissue at the GE junction. Once removable attachment 42 is severed at separable portions of both struts 20c, 20d cardiac portion 16 can be distally withdrawn thus axially liberating the struts from the captured tissue at the GE junction.

As discussed above, cardiac portion 16 will be in the stomach and can be removed transorally. In addition to a separate chain stich 46 for each strut as shown, it is possible to extend the chain stitch to encompass separable portions of both struts (not shown) so that the chain stitch filament need be severed only once to break both struts free of the wall portion. Also, it is possible that tissue bridging may only occur at one of strut pairs 20a, 20b, such as strut 20b or one of strut pairs 20c, 20d positioned against the GE sphincter at the angle of HIS. As such, removable attachment 42 may be provided for only one strut.

Figure 10:
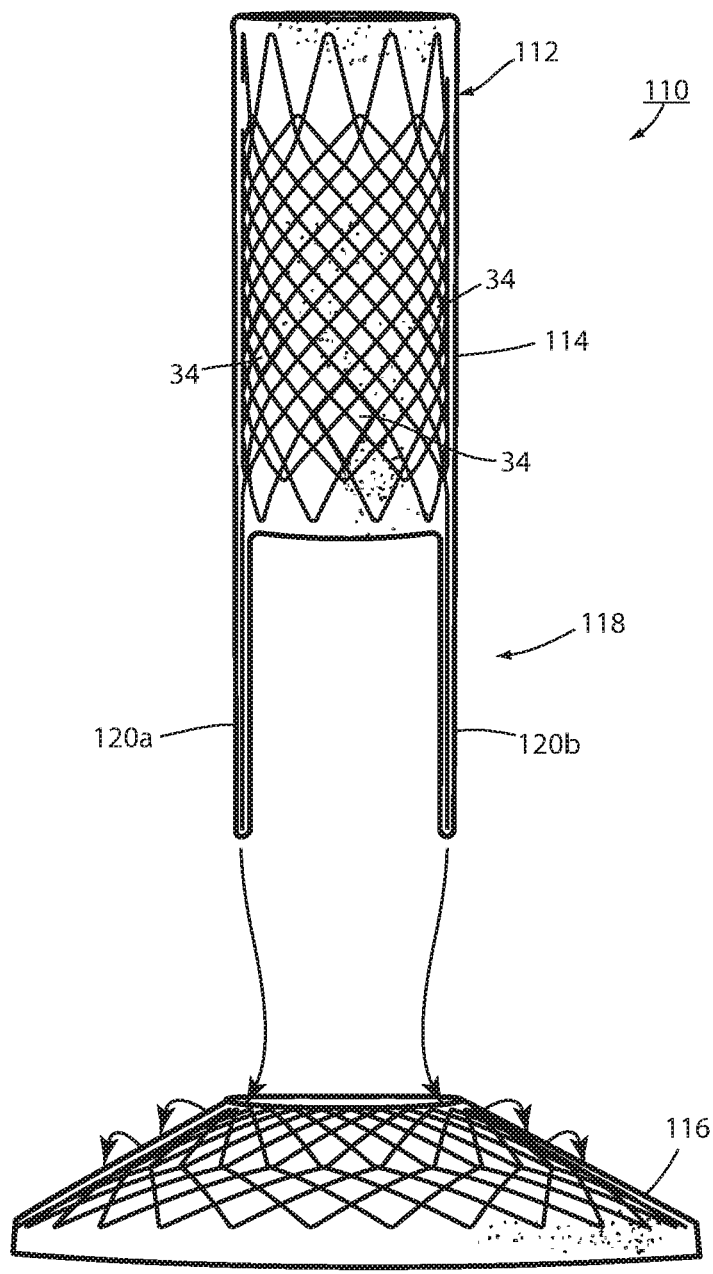
FIG. 10 is the same view as FIG. 7 of an alternative embodiment.
Figure 10A:
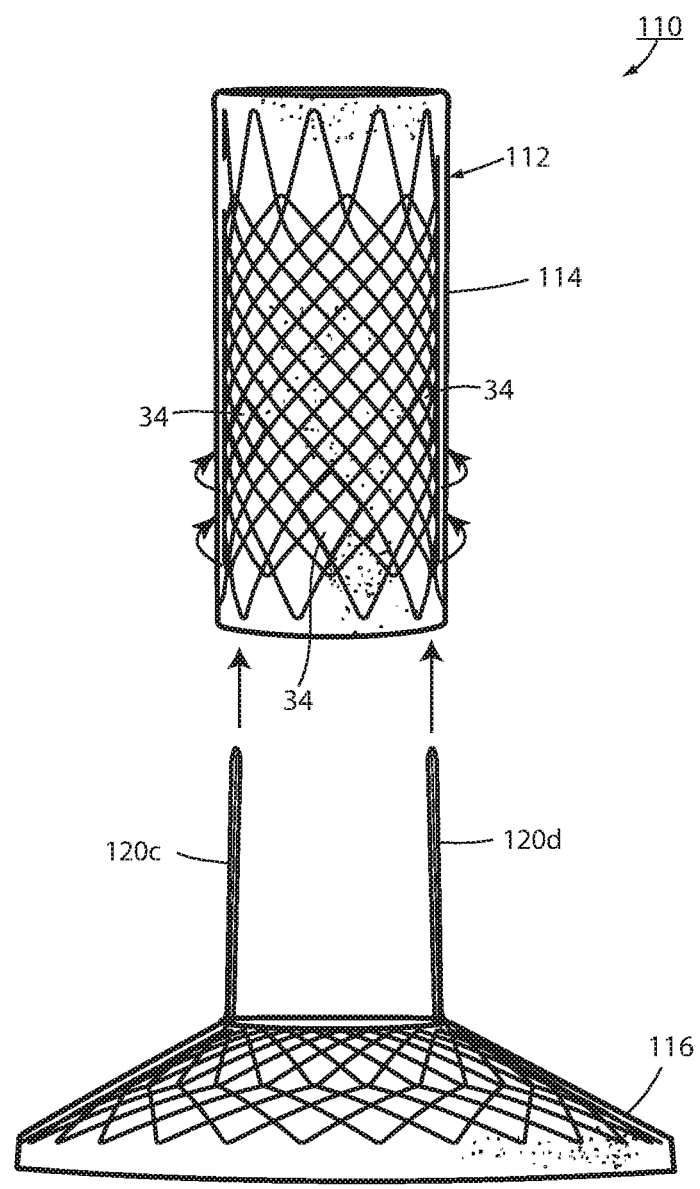
FIG. 10A is the same view as FIG. 10 of an alternative embodiment thereof.

In an alternative embodiment, an intraluminal device 110 includes a wall 112 defining an esophageal portion 114 configured to the size and shape of a portion of the esophagus, a cardiac portion 116 configured to the size and shape of a portion of the cardiac portion of the stomach and a connector 118 (FIGS. 10-13) of which at least a portion passes through the GE junction. Tissue ingrowth openings 134 provide long-term fixation. Intraluminal device 110 is essentially the same as device 10 except that connector portion 118 is removably connected with wall 112 by an alternative removable attachment 142. In FIG. 10, separable portions of struts 120a, 120b making up connector portion 118 extend over some of intersections 144 of the mesh 132 of cardiac portion 116 and under other ones of the intersections 144 at cardiac portion 116 as seen in FIGS. 10-13. In FIG. 10A, separable portions of struts 120c, 120d extend over some intersections of the mesh of esophageal portion 114 and under other ones of the intersections at the esophageal portion 114 of wall 112.

Figure 11:
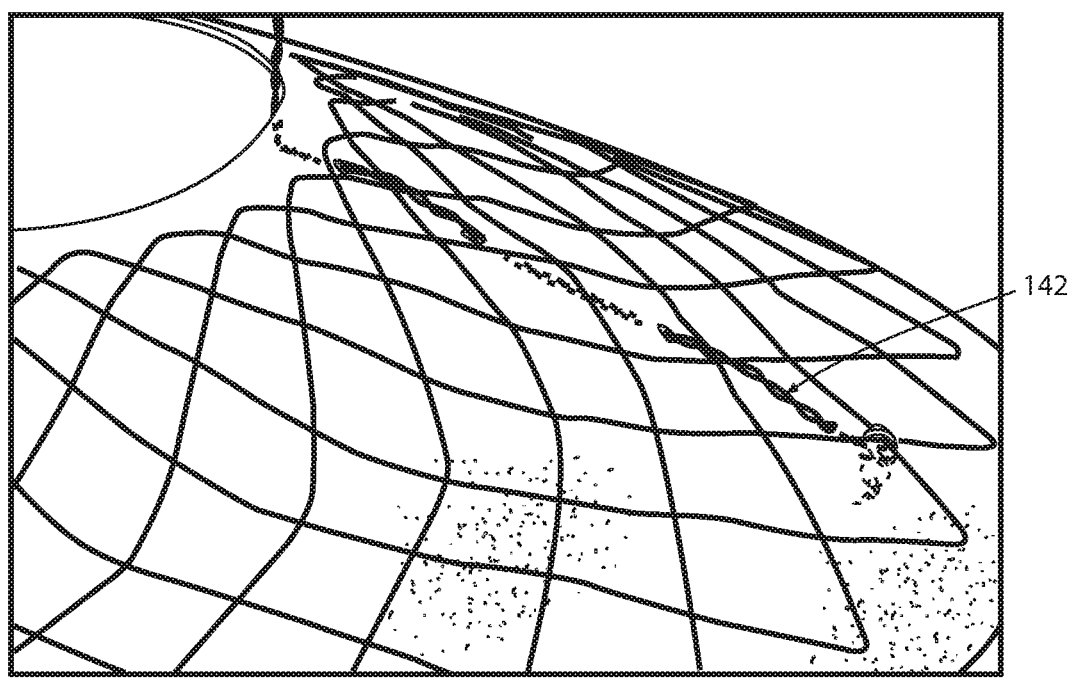
FIG. 11 is a perspective view taken from the side and proximal or top showing a removable attachment between the connector portion and the cardiac portion of the embodiment in FIG. 10.
Figure 12:
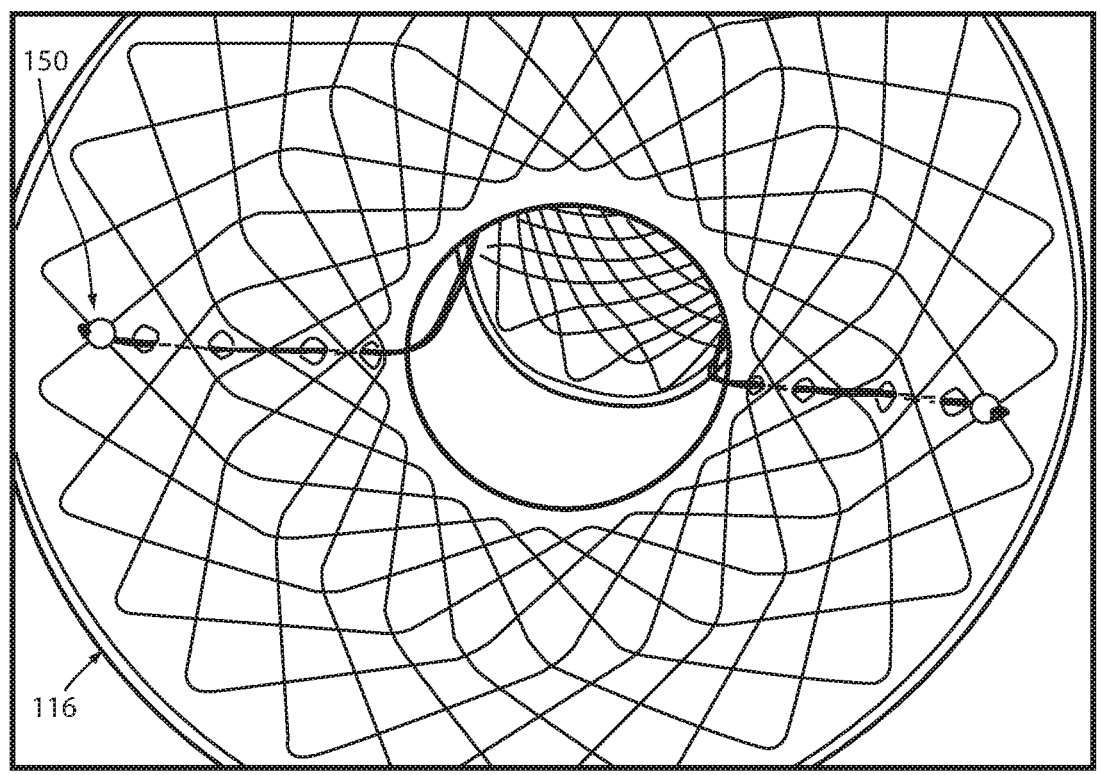
FIG. 12 is a bottom or distal plan view of the removable attachment in FIG. 11.
Figure 13:
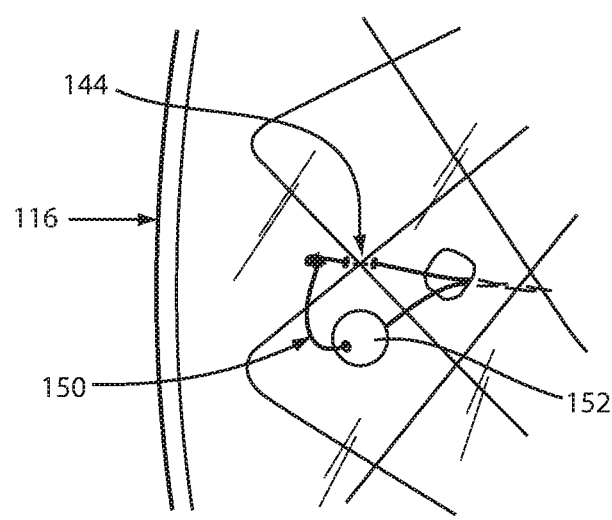
FIG. 13 is an enlarged view of the severable knot in FIG. 12.

Removable attachment 142 includes a severable knotted filament 150 at a distal end of each strut secures an end of the separable portion of the strut to the wall as seen in FIGS. 11-13. In this manner, severing of filament 150 allows each strut to pull away from the wall portion. The severable filament 150 may include an extender, such as a bead 152, to enhance access to the filament to assist in severing the filament. Bead 152 is strung on filament 150. Filament 150 may extend between both separable ends of the struts so that the filament needs to be severed at one place to free both struts from the wall portion.

Figure 14:
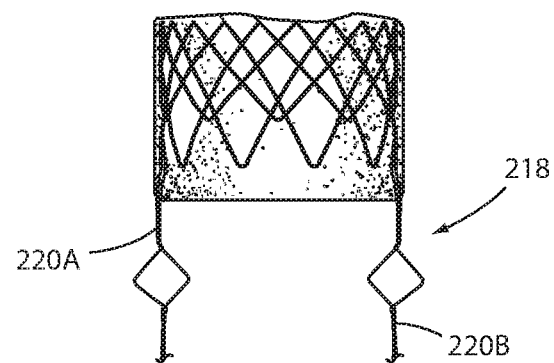
FIG. 14 is a side elevation of an alternative embodiment of a connector portion.

It should be understood that the tissue bridging over struts 20a, 20b, 20c, 20d, 120a, 120b, 120c, 120d which are elongated filaments that provide a wall characteristic that fixes the wall of the respective struts to the GE region through growth of tissue, can be useful as all or part of long-term fixation of device 10, 110. Such long-term fixation may be enhanced by adding length to similar struts 220a, 220b shown in FIG. 14. This may be accomplished by providing a knee to the strut, such as branching to the filaments as seen in FIG. 14. This may be accomplished by leaving the filaments non-twisted so that each filament forms a separate bridge that bows outwardly. Once the attachment to the wall portion (not shown in FIG. 14) is severed, the multiple filament branches to the strut can be individually pulled through the same opening in the mucosa caused by the bridging. Struts 20a, 20b, 20c, 20d 220a, 220b, 220c, 220d can have an outward knee to further engage the mucosa to promote tissue bridging.

Figure 15:
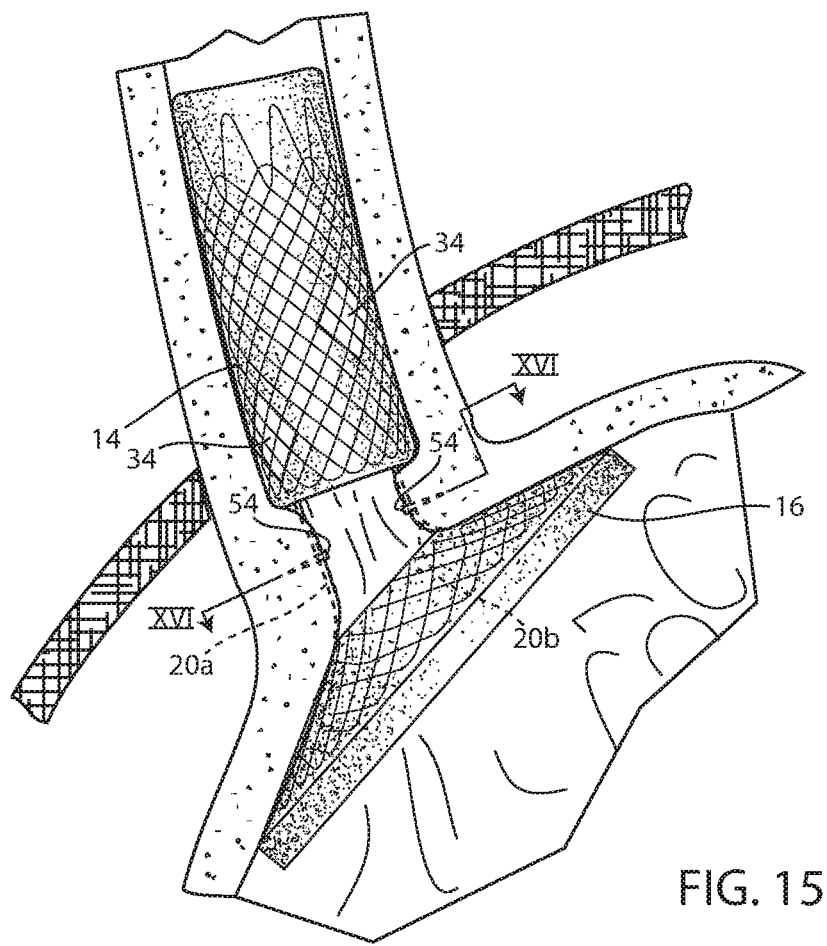
FIG. 15 is a side elevation of an alternative embodiment showing enhancement of mucosal bridging.
Figure 16:
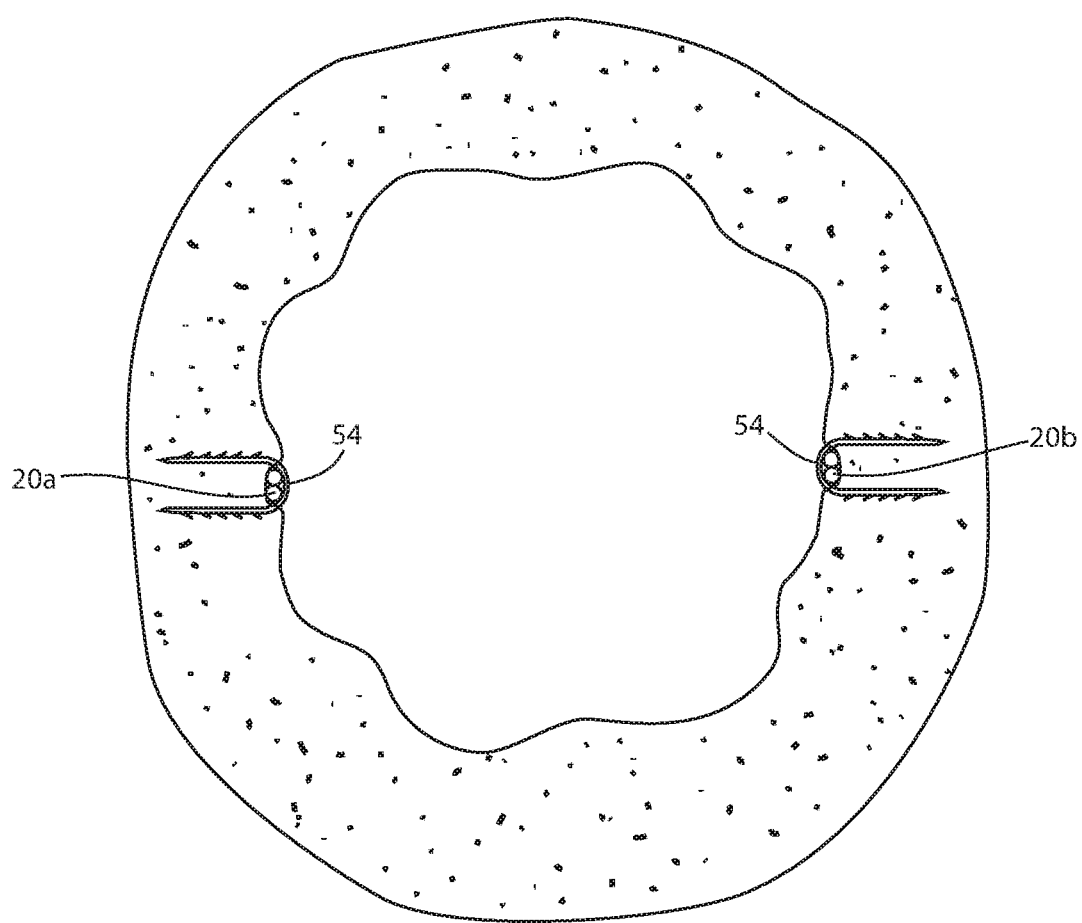
FIG. 16 is a sectional view taken along the lines XVI-XVI in FIG. 15.
Figure 17:
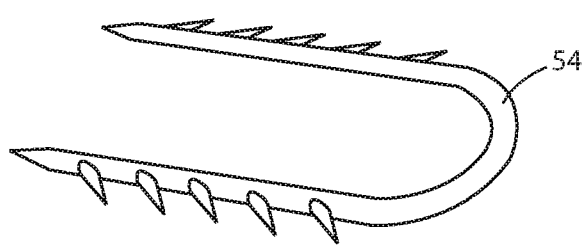
FIG. 17 is a perspective view of a clip.
Figure 18:
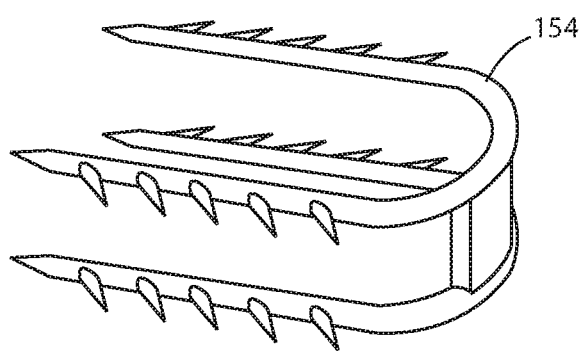
FIG. 18 is the same view as FIG. 17 of an alternative embodiment thereof.

Also, short-term and/or long-term fixation using the struts can be enhanced by applying tissue penetrative fasteners in the form of retainers 54 to the bridging mucosa (FIGS. 15-17). Retainers 54 include a U-shaped body having a pointed end with barbs 55. This allows the retainer to be inserted through the mucosa onto the muscular and the barbs to hold the retainer in place. Retainers 54 can be bioabsorbable so that they fall away after the passage of time when mucosal bridging is secure. Alternatively, retainers 154 include coupled U-shaped portions, each with barbs 155 in order to enhance attachment to the muscular as seen in FIG. 18. Application of suction to the esophagus of the recipient will tend to cause the tissue of the EG junction to come together around the respective strut to assist in placement of retainers 154 to bring the tissue portions together around the strut to facilitate tissue capture of the strut using the principles disclosed in commonly assigned U.S. Pat. No. 8,894,670, the disclosure of which is hereby incorporated herein by reference in its entirety.

Other forms of tissue penetrating fasteners can be used, such as EZ clip or a quick-clip, both available from Olympus. In addition to promotion of tissue bridging over the strut(s) 20a, 20b, 20c, 20d, 120a, 120b, 120c, 120d, the retainers 54, 154 may provide resistance to distal migration of esophageal member 14. This helps to provide tension on the struts, thus ensuring cardiac member 16, 116 is in contact with the cardiac portion of the stomach. Thus, clip 54, 154 may provide both immediate short-term fixation of the bariatric device and promote long-term fixation via fusion of tissue bridging struts 20a, 20b, 20c, 20d, 120a, 120b, 120c, 120d.

An intraluminal device 210 is shown in FIGS. 19-23 in which another technique is shown for fixation of the intraluminal device against peristalsis in the lumen. Device 210 includes a wall 212 defining an esophageal portion 214 having a size and shape corresponding to a portion of the esophagus at the GE region, a cardiac portion 216 having a size and shape corresponding to a portion of the cardia or a cardiac portion of the stomach, and a connector 218 connecting the esophageal portion to the cardiac portion. At least a portion of connector 218 passes through the GE junction. Connector 218 is made up of two elongated struts 220a, 220b, both of which pass through the GE junction. The struts elongated shape provides a wall characteristic that provides, at least in part, long-term fixation of wall 212 to the GE region though growth of tissue around each strut. Struts 220a, 220b include a biocompatible coating, such as silicone, or the like, that allows the struts to be axially separated from the GE junction once severing of the removable connector (not shown in FIG. 19) separates the strut from the wall portion 212 in the manner previously described.

An alternative issue penetrating fastener 256 around each strut 220a, 220b includes a series of tissue penetrating barbs 257 that are capable of penetrating mucosa, submucosa, and/or muscular at the GE junction when pressed against the tissue. Penetrating barb 257 may have fishhook, or arrowhead, features to avoid withdrawal of the barbs once inserted. Fastener 256 may be formed around the strut as part of manufacture or may be a separate device as shown in FIG. 20 having a slit that allows it to be positioned around the strut at deployment.

In addition to the dimensions of each strut providing a wall characteristic that causes tissue to grow around the strut, each fastener 256 may have a wall characteristic 259 facing away from the tissue of the GE junction that enhances long-term fixation of wall 212 to the GE region through promoting growth of tissue around the respective strut. Wall characteristic 259 may be a roughened or fenestrated surface, a surface impregnated with a tissue growth agent, or the like. Wall characteristic 259 may include bars similar to barbs 257 such that application of suction to the esophagus of the recipient tends to draw the tissue of the GE junction around the wall characteristic 259 where it is ensnared by the barbs of wall characteristic 259 to further enhance short-term fixation. Fastener 256 may be made in whole or in part from a bioabsorbable material to resorb after tissue grows around the strut to provide long-term fixation of device 210. The resorption of the fastener 256 avoids fastener 256 from impeding axial withdrawal of the struts for device explantation.

Another tissue penetrating fastener 258 having tissue penetrating barbs 257 may be at a portion of esophageal member 214, such as at its distal rim, in order to provide additional temporary fixing of device 210 at the GE region. Fastener 258 is shown formed or otherwise attached to a distal rim of esophageal portion 214 but could be located at any portion of esophageal portion 214. Fastener 258 only provides temporary fixing of device 210 and therefore does not include a wall characteristic 259 that enhances long-term fixing of wall 212 to the GE region. Fastener 258 is made in whole or in part from bioabsorbable material in order to resorb after long-term fixation is in place to avoid interference with explantation of device 240.

Figure 23:
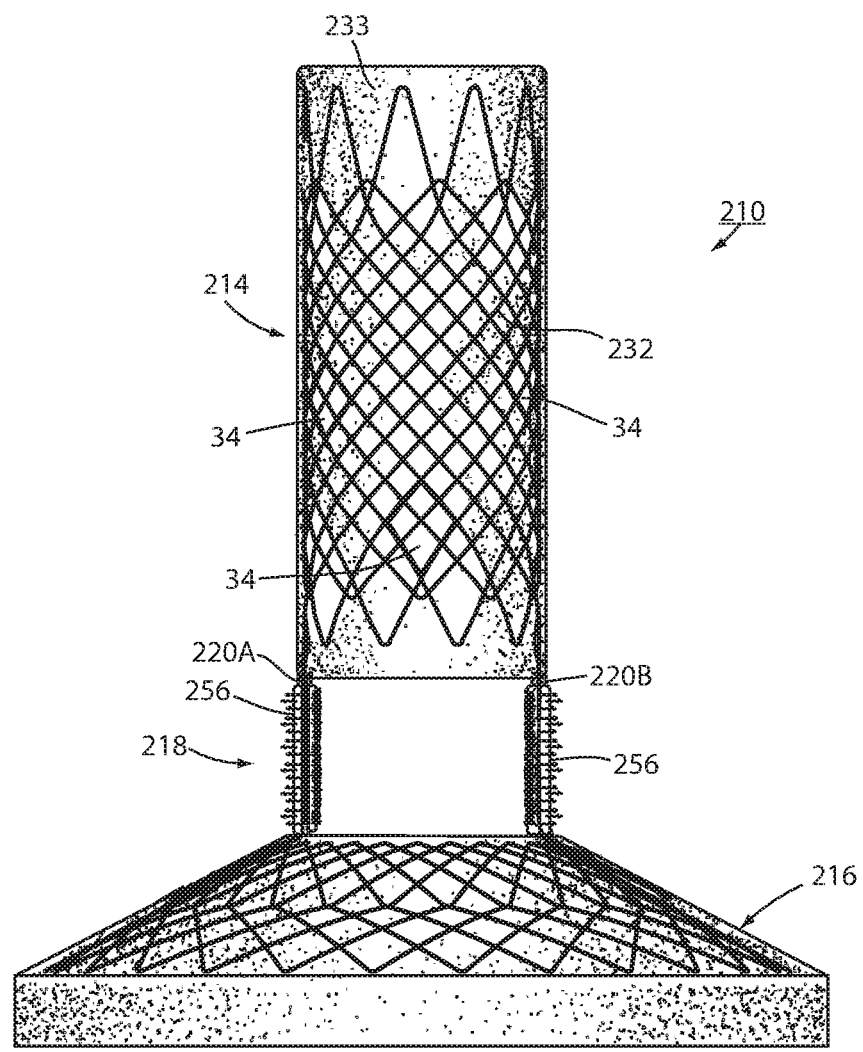
FIG. 23 is the same view of the same device of FIG. 19 of an alternative embodiment.

As seen in FIG. 23, device 210 may include a fastener 256 at one or both struts 220a, 220b making up connector 218, but not include a fastener 258 at the esophageal portion 214. Of course device 210 may include a tissue penetrating fastener 258 without a combination temporary and permanent fixing device 256 since the elongated slender nature of struts 220a, 220b are a wall characteristic that fixes wall 212 to the GE region through growth of tissue to provide long-term fixation.

Figure 24:
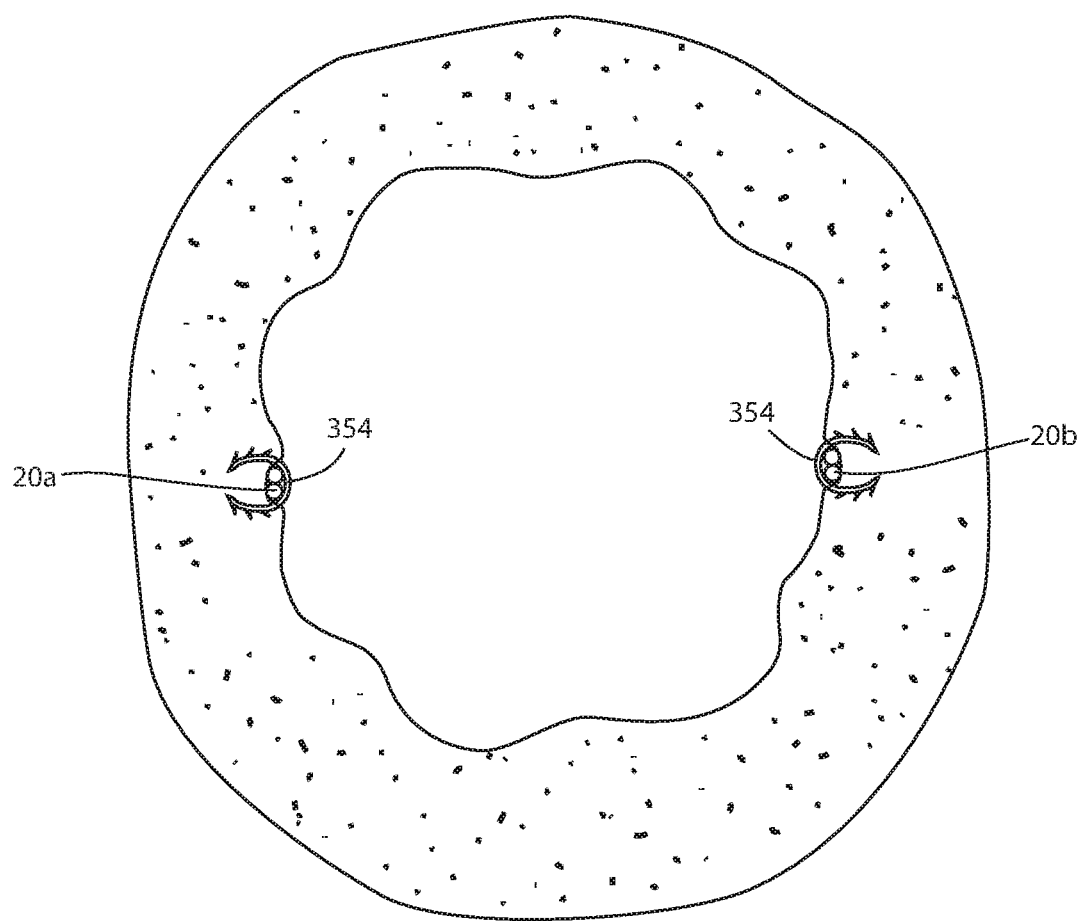
FIG. 24 is the same view as FIG. 16 of an alternative embodiment.

An alternative retainer 354 shown in FIG. 24 is a clip that closes around the strut 20a, 20b, 20c, 20d, 2120a, 120b, 120c, 120d, or which only struts 20a and 20b are shown, after the device 10 is positioned at the GE region. Clip 354 may be spring-loaded or made from memory material to close around the strut upon being positioned in the tissue or may be mechanically deformed by a mechanism that is endoscopically deployed. Suction applied to the esophagus of the recipient may be applied to assist in drawing tissue around the struts to facilitate a clip being inserted into the tissue.

FIG. 26 illustrates another tissue penetrating fastener 258b that may be used in whole or in part for short-term fixation of device 210 against distal migration. Fastener 258b may be placed at a proximal end portion of esophageal portion 214. Fastener 258b has barbs 257b that at least partially penetrate the tissue of the esophagus to provide short-term fixation. Fastener 258b may be made in whole or in part from a resorbable material in order to be absorbed in the recipient after long-term fixation has occurred. Barbs 257b are illustrated as being distally angled so that device 210 can be adjusted proximally during deployment without impediment from the bars which are still capable of resisting distal migration.

Figure 27:
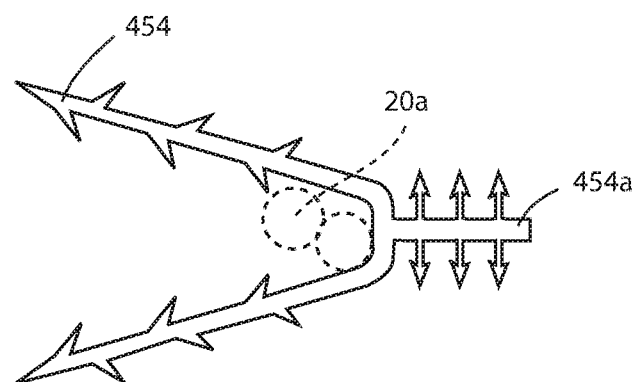
FIG. 27 is a plan view of an alternative embodiment of a clip.
Figure 28:
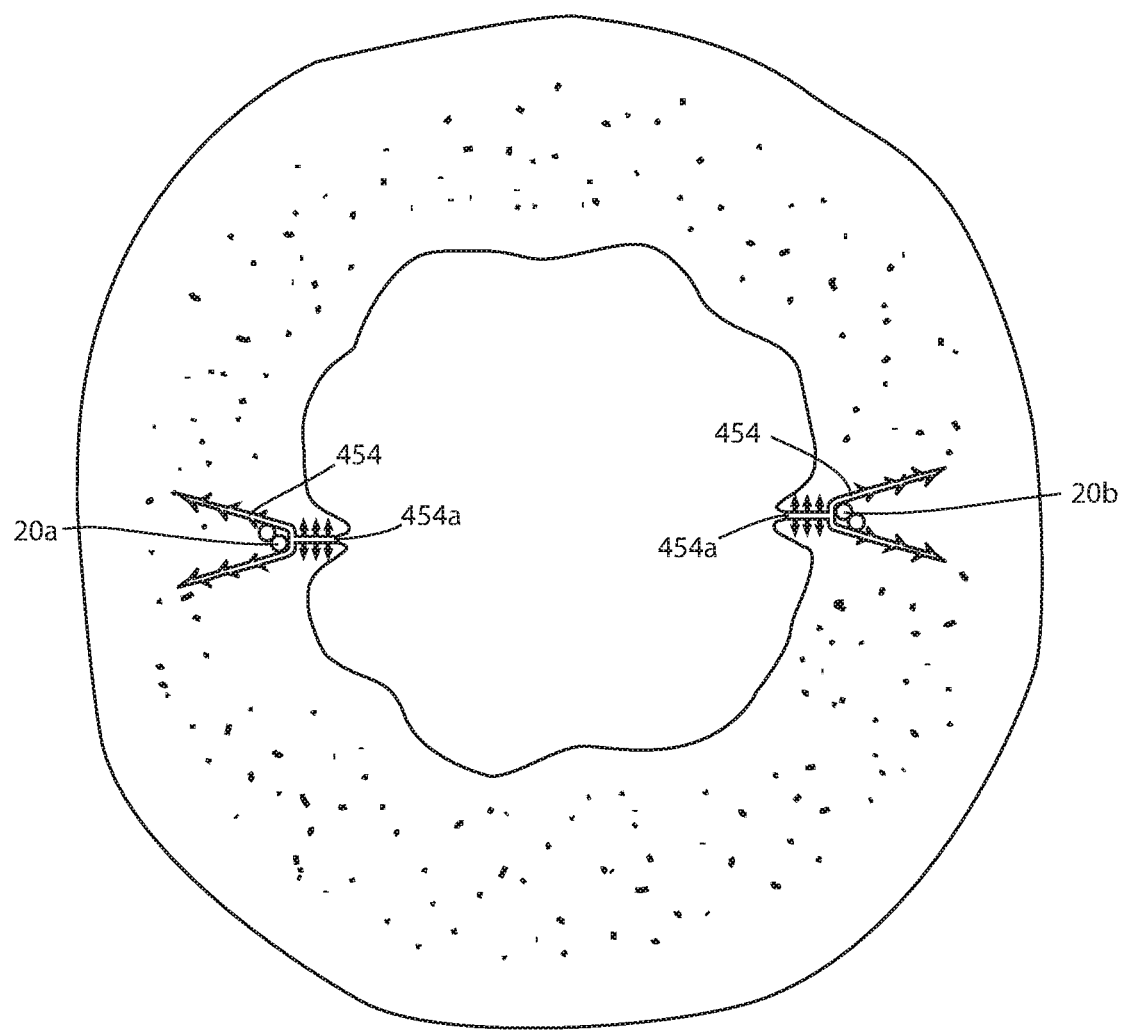
FIG. 28 is the same view as FIG. 24 showing the clip in FIG. 27 applied.

FIGS. 27 and 28 illustrate yet another alternative tissue penetrating retainer 454 that can be used for short-term fixation of the intraluminal device 10, 110, 210. Retainer 454 is positioned along a strut up against the esophageal portion. Retainer 454 is barbed to be retained. In the tissue of the GE junction as shown in FIG. 28 includes a tissue attachment portion 454a. After retainer 454 is over the strut and inserted into the tissue (either as part of positioning the device or after the device is positioned), suction may be applied to the esophagus which will tend to draw tissue around the strut where it will be retained by barbs or other surface of tissue attachment portion 454a.

Figure 25:
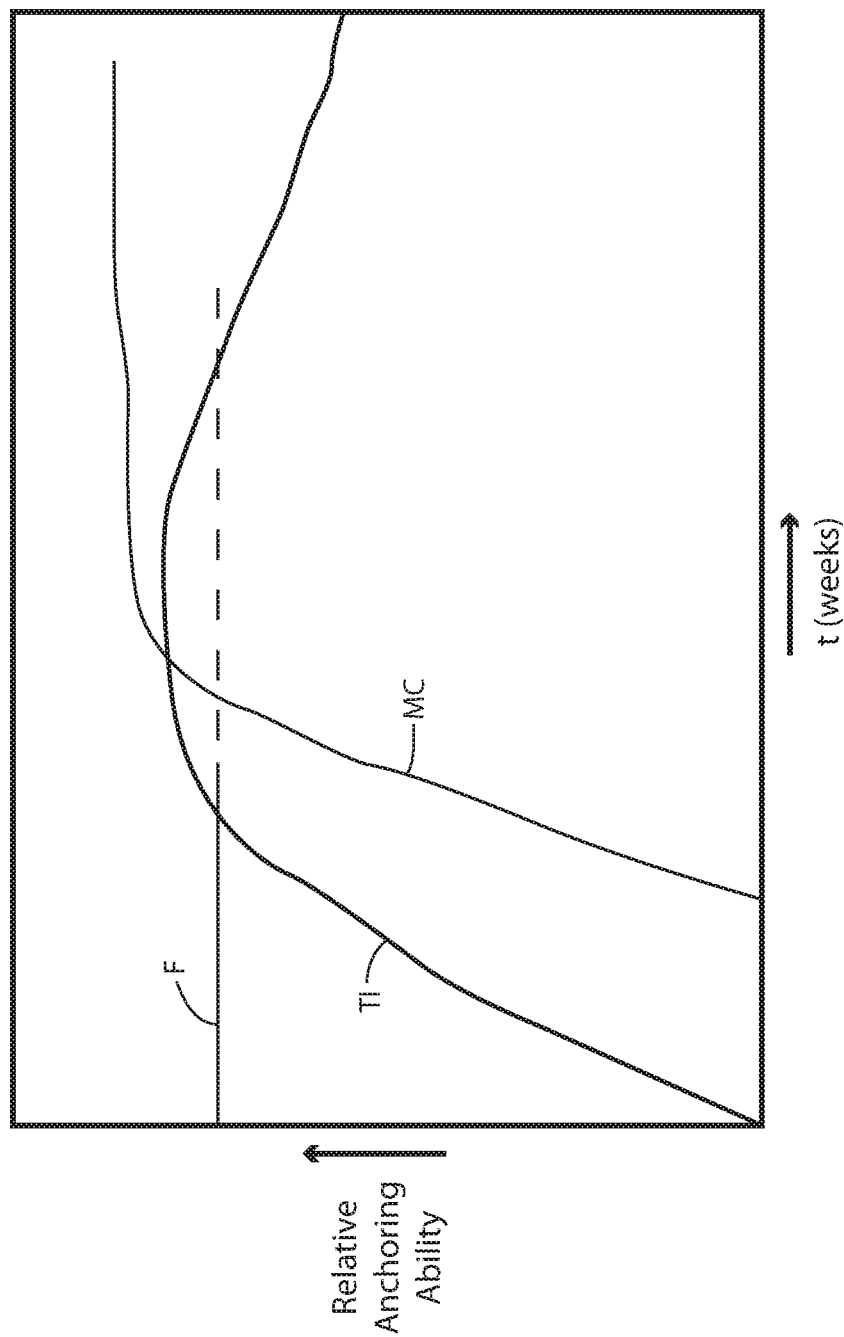
FIG. 25 is a chart illustrating relative anchoring strength of different anchoring techniques over time.

Thus, it is seen that aspects of the present invention encompass short-term and long-term fixation of an intraluminal device, such as a bariatric device, in a lumen, such as the gastro-esophageal region of the recipient. The long-term fixation uses the body's response to the presence of the device to provide long-term fixation. Short-term fixation, such as one or more tissue penetrating fasteners, provide fixation of the device while long-term fixation develops. Once long-term fixation develops, the short-term fixation may slough off or be absorbed as it is no longer needed. Even multiple different types of long-term fixation may be provided in order to provide optimal fixation at different times after deployment. For an example, FIG. 25 illustrates relative fixation, shown on the Y-axis for different time intervals after deployment, shown on the Y-axis. When the device is deployed, at the origin of the graph, temporary fixation F maintains the intraluminal device in place. After deployment, the tissue ingrown TI begins to develop and increases over time. Sometime after deployment, temporary fixation F may be eliminated, such as by absorption of resorbable sutures or filament loops, as depicted by the dashed horizontal line. By that time, the tissue ingrowth TI should be sufficiently strong to provide long-term fixation. An additional form of long-term fixation may be provided by mucosal capture MC around the struts of the bariatric device. While the mucosal capture MC may take longer to develop than the tissue ingrowth TI, it may provide long-term fixation even if the tissue ingrowth fixation TI weakens over time.

It should be understood that FIG. 25 is intended to illustrate conceptual relationships and is not based upon physical measurements. It should also be understood that the timeline in FIG. 25 may be measured over days, weeks or months. However, it is expected that tissue ingrowth TI or mucosal capture MC should be sufficient to provide fixation by itself within about four (4) days to one or more weeks.

It may also be possible to eliminate tissue ingrown TI and rely exclusively on mucosal capture MC in order to provide long-term fixation. Such alternative may include using one of the illustrated retainers around one or both struts in order to provide short-term fixation while long-term fixation develops, such as by mucosal capture MC around each of the struts. By providing both short-term and long-term fixation at the struts, the intraluminal device should be simpler to deploy and explant. Deployment may occur by the insertion of a retainer clip at one or both struts or even by a self-deploying retainer that penetrates tissue at the GE junction upon positioning of the device in the lumen of the recipient. With long-term fixation provided at the struts alone, the device can be explanted by separating the separable struts and axially retracting the struts from the GE junction by proximally withdrawing the esophageal member from the esophagus. The cardiac member can then easily be retrieved from the stomach. Because tissue ingrowth is not employed in such embodiment, there is no need to remove tissue from the tissue ingrown zones.

The intraluminal device 10, 110, 210 may be made adjustable in order to adjust or titrate the amount of stress on the cardiac portion of the stomach, such as by using a bladder or bladders on the proximal surface of the cardiac portion using the principles disclosed in International Application Publication No. WO2015/031077, the disclosure of which is hereby incorporated herein by reference in its entirety. Besides providing for adjustability, such bladder(s) may be filed with a fluid made of a lighter-than-air gas, such as helium, hydrogen, or the like, in order to assist in urging the cardiac member against the cardiac portion of the stomach in order to at least partially provide short- or long-term fixation.

Figure 29:
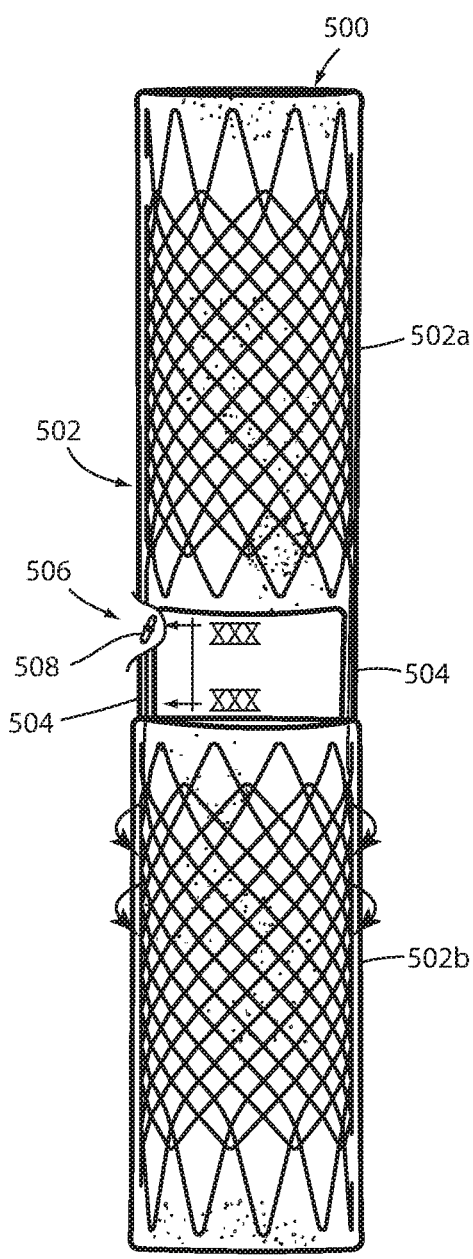
FIG. 29 is a side elevation of an alternative embodiment of an intraluminal device.
Figure 31:
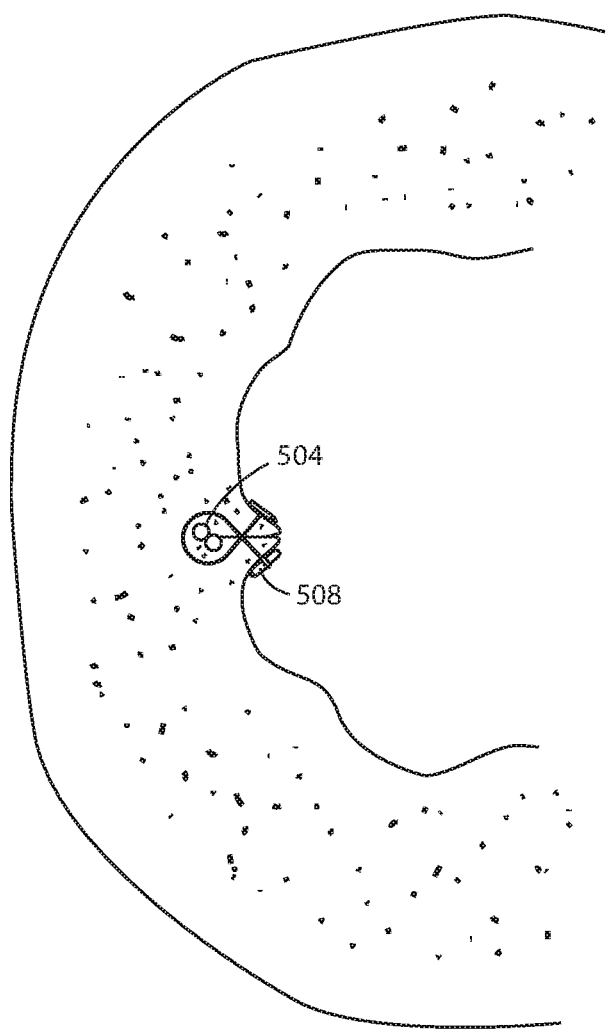
FIG. 31 is a sectional view taken along the lines XXXI-XXXI in FIG. 30.
Figure 32:
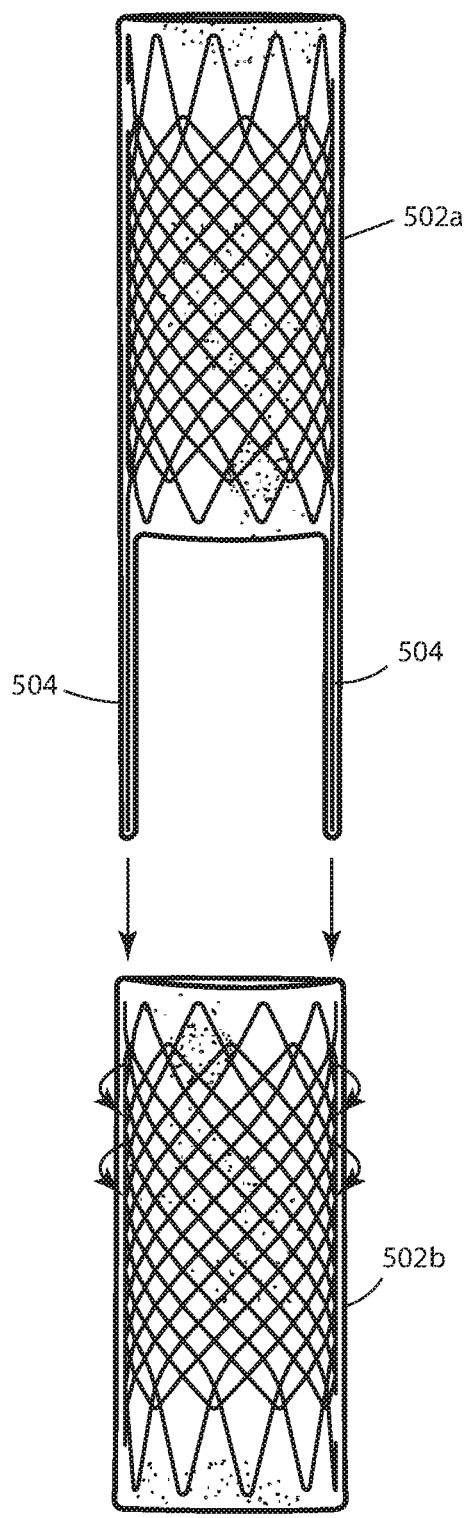
FIG. 32 is a view of the device in FIG. 29 illustrating assembly thereof.
Figure 33:
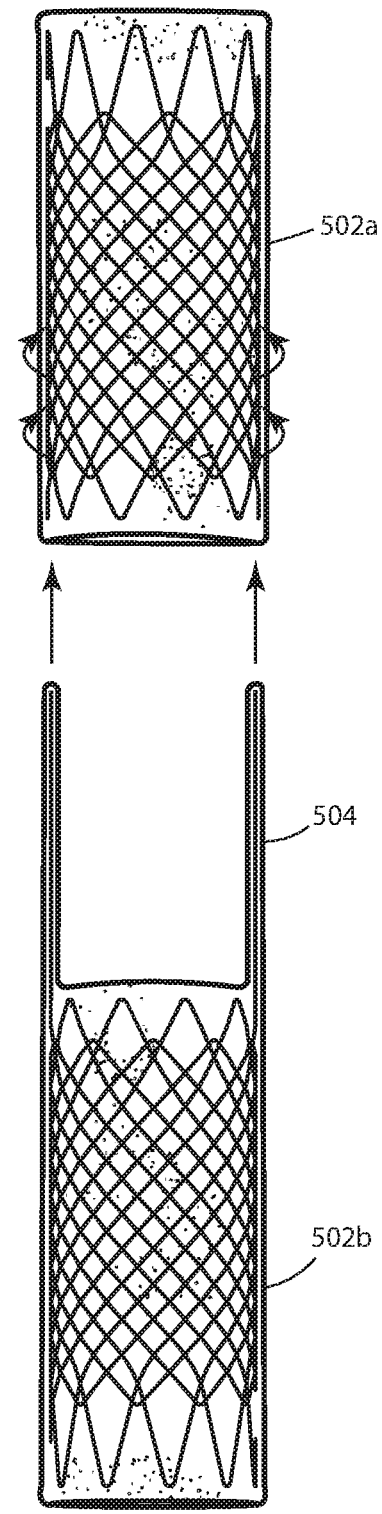
FIG. 33 is an alternative view of the device in FIG. 29 illustrating assembly thereof.

An intraluminal device 500 is adapted to be positioned in a lumen that experiences peristalsis such as shown in FIG. 31. The lumen may be an esophagus, a colon, nasal passage, or other lumen that experiences peristalsis and therefore is subject to distal and/or proximal migration. Device 500 includes a wall 502 that is configured to the size and shape of a portion of the lumen in which the device is intended to be implanted and includes a first separable wall portion 502a and second separable wall portion 502b (FIG. 29). Device 500 further includes a core 504. Core 504 is removably connected with wall portion 502a or 502b and adapted to be disconnected in situ from the portion 502a of the wall as illustrated by the arrows in FIG. 29. FIG. 32 illustrates each core 504 fixedly connected with wall portion 502a and removably connected with wall portion 502b in a manner that the core can be disconnected in situ from wall portion 502b. FIG. 33 illustrated each core 504 fixedly connected with wall portion 502b and removably connected with wall portion 502a in a manner that the core can be disconnected in situ from wall portion 502a.

Core 504 is an elongated narrow body that is capable of tissue, such as mucosa, lining the lumen encompassing or bridging the body of the core during deployment or implantation of the intraluminal device in the lumen. The core can be of any cross sectional shape, can be rigid or flexible, can be a tension member or not and can be made of a variety of materials such as suture material, medical grade titanium, nitinol coated with a biological grade cover, or the like. Examples of cores are struts 20a, 20b in FIG. 1.

Core 504 is configured to be positioned against the lumen when wall 502 is positioned in the lumen. In this matter tissue envelopes the core during implantation of the device as seen in FIG. 31. The tissue of the lumen where the core is to be positioned against the lumen may be disrupted to promote the tissue enveloping the core. Such disrupting of the tissue may be by using cauterization, ultrasound therapy and/or cryo-therapy or the like. Core 504 is configured to be axially removable from the tissue enveloping the core when core 504 is disconnected in situ from the portion 502a and/or 502b of wall, as shown by the arrows in FIG. 29 in order to explant the intraluminal device 500 from the lumen.

The two separate wall portions 502a and 502b that are connected together with cores 504 in order to form wall 502 of intraluminal device 500. Cores 504 be removably connected with at wall portions 502a, 502b. Cores 504 may be axially removable from the lumen encompassing each core, as seen in FIG. 31 in order to explant the intraluminal device from the lumen when the core 504 is disconnected from either wall portion 502b in the configuration illustrated in FIG. 32 or wall portion 502a in the configuration illustrated in FIG. 33. In this embodiment with two or more separable wall portions connected together with the cores, the cores may be referred to as connectors, a struts, or a tension members because the cores transfer force between the wall portions which would otherwise separate in situ.

Figure 30:
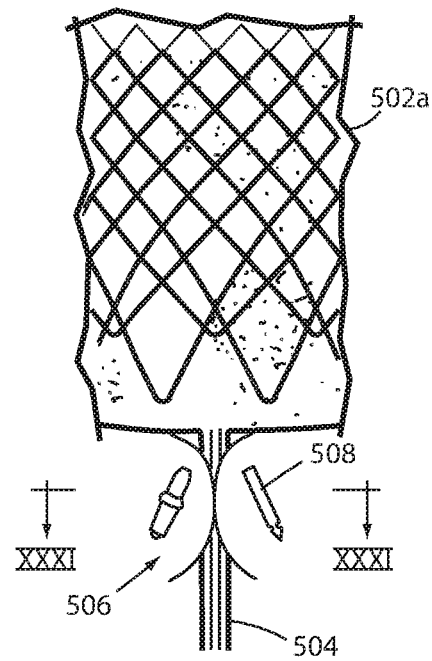
FIG. 30 is a sectional view taken along the lines XXX-XXX in FIG. 29.

A fastener 506 may be provided to fasten 504 core to the lumen in order to fix intraluminal device 500 in the lumen. The fastener may be a suture 508 as illustrated in FIG. 30 and FIG. 31. Suture 508 is applied around 504 core when applied to the lumen. A portion of lumen tissue is wrapped around core 504 when applying the suture around the core. This provides immediate fixation of the intraluminal device in the lumen against migration. Also, the wrap of the tissue around the core speeds the tissue enveloping the core to provide long term fixation of the intraluminal device. The fastener may be adapted to be applied intraluminally. In the illustrated embodiment, suture 508 is an intraluminal suturing device marketed by Apollo Endosurgery.

As best seen in FIG. 30 fastener 506 is at an upstream end portion of the core with respect to predominant peristaltic movement in the lumen. With the fastener as close as possible to the connection of the core with wall portion 502a there is minimal sippage of core 504 with respect to fastener 506 before wall portion 502a engages the fastener and thus restricts further movement.

Figure 34:
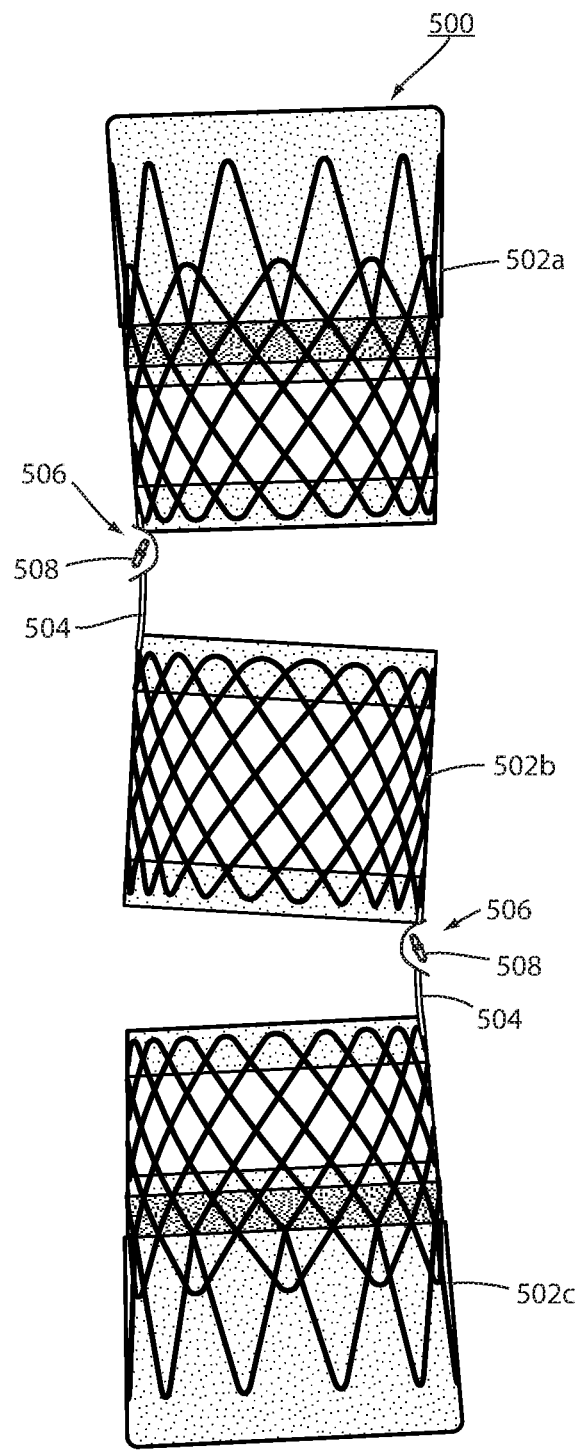
FIG. 34 is a side elevation of an alternative embodiment of an intraluminal device.

Alternatively, fastener 508 may be a clip such as clip 54, 154, 354, or 454. It is also possible to have only one core 504 instead of a pair and rely on the shape of the lumen to maintain the overall form of the intraluminal device as shown in FIG. 34. Also, more than two separate wall portions 502a, 502b, and 502c and be used as also shown in FIG. 34.

Core 504 may be connected with wall portion 502a and/or 502b with a removable attachment 42, 142 (FIGS. 8-13). Core 504 is separable from the respective wall portion by removing the removable attachment 42, 142. The removable attachment may be made of a severable filament 150. An enlarged member such as a bead 152 may be on the at least one core to space severable filament 150 from the wall portion for access to the filament as best seen in FIG. 13. The at least one core may be coated with a bio-compatible material, such as silicone that extends around the at least one core. Wall 502 may be formed into an esophageal stent, an anti-reflux device, a nasal gastric tube, an intestinal sleeve, a bariatric device, a metabolic disease treatment device, or the like.

Figure 35:
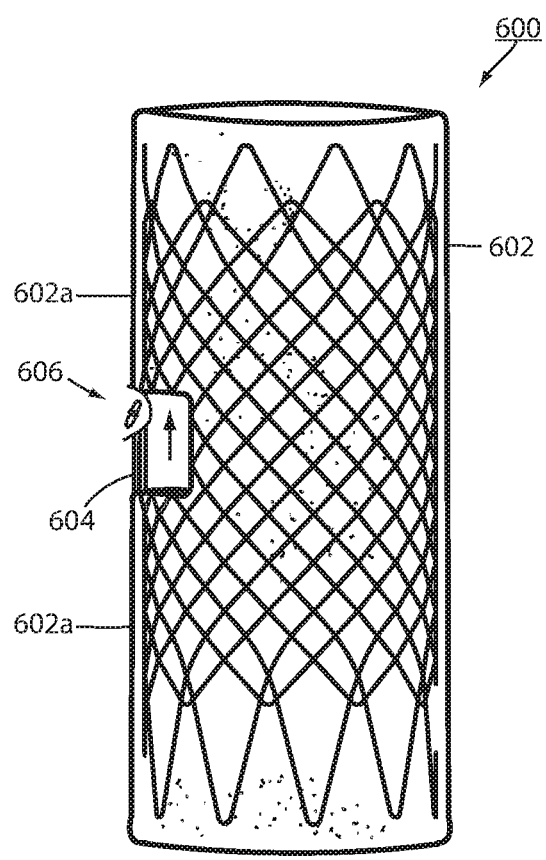
FIG. 35 is a side elevation of an alternative embodiment of an intraluminal device.
Figure 36:
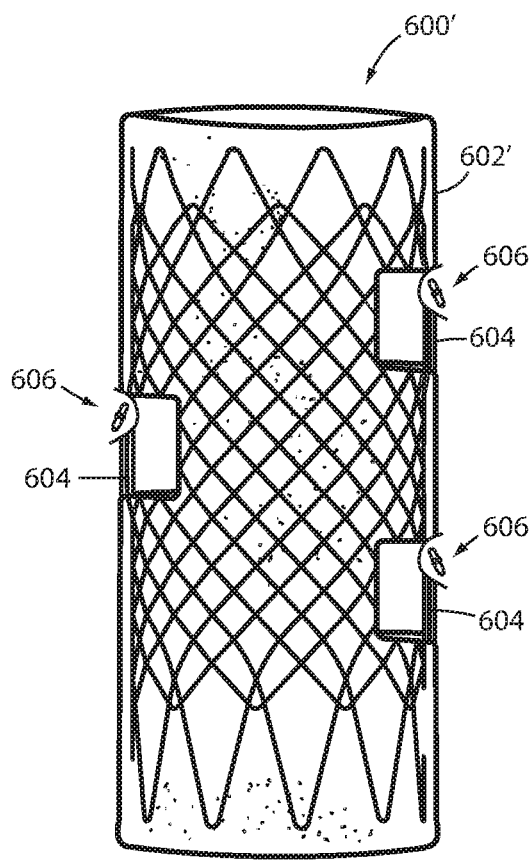
FIG. 36 is a side elevation of an alternative embodiment of an intraluminal device.

An intraluminal device 600 has a unitary wall 602 with at least one core 604 that is removably connected with a portion 602a of wall 602 by being configured to be axially movable with respect of another portion 602b of the wall (FIG. 35). The at least one core may include at least two cores 604 that are each removably connected with a different portion of the wall 602' by being configured to be axially movable with respect to other portions of wall 602' as seen in FIG. 36. With core(s) 604 in the axial extended position illustrated in FIGS. 35 and 36 the intraluminal device 600, 600' is deployed to the lumen. A fastener 606 is applied to each core in the manner previously described. Optionally, a suction may be applied to the interior of wall 602, 602' to assist in drawing the mucosa of the lumen around the core. After device 600, 600' has been implanted for a period of one week to a number of months, sufficient to perform its intended function, and is ready to be explanted, core(s) 604 are removed from the tissue encompassing the core(s). This is accomplished by endoscopically severing the filament making up attachment 42, 142 and retracting the core(s) into wall portion 602b, which is upward in FIGS. 35 and 36. This axially withdraws the core(s) from the tissue encompassing the core so that device 600, 600' can be explanted without needing to incise the tissue encompassing the core.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A method of fixation of an intraluminal device in a lumen that experiences peristalsis, said method comprising:
the intraluminal device having a wall configured to the size and shape of a portion of the lumen and at least one core, said at least one core removably connected with a portion of said wall and adapted to be disconnected in situ from the portion of the wall;
positioning the wall in the lumen including positioning the at least one core against the lumen whereby tissue grows around the at least one core with passage of time during implantation of the intraluminal device in the lumen; and
disconnecting in situ the at least one core from the portion of the wall by axially moving said at least one core with respect to the portion of said wall and axially removing the at least one core from the tissue around the at least one core in order to explant the intraluminal device from the lumen.

2. The method of fixation of an intraluminal device as claimed in claim 1 wherein said at least one core comprises at least two cores that are each removably connected with a different portion of the wall and disconnecting said at least two cores by axially moving said at least two cores with respect to other portions of said wall.

3. The method of fixation of an intraluminal device as claimed in claim 1 wherein said at least one core comprises at least two cores that are each removably connected with a different portion of the wall.

4. A method of fixation of an intraluminal device in a lumen that experiences peristalsis, said method comprising:
the intraluminal device having a wall configured to the size and shape of a portion of the lumen and at least one core, said at least one core removably connected with a portion of said wall and adapted to be disconnected in situ from the portion of the wall;
positioning the wall in the lumen including positioning the at least one core against the lumen whereby tissue grows around the at least one core with passage of time during implantation of the intraluminal device in the lumen; and
disconnecting in situ the at least one core from the portion of the wall and axially removing the at least one core from the tissue around the at least one core in order to explant the intraluminal device from the lumen, wherein said wall comprises at least two separate wall portions that are connected together with said at least one core and wherein said at least one core is removably connected with at least one of said at least two wall portions including axially removing said at least one core from the lumen in order to explant the intraluminal device from the lumen tissue around the at least one core including disconnecting the at least one core from said at least one of said at least two wall portions and separately removing said at least two separate wall portions from the lumen.

5. The method of fixation of an intraluminal device as claimed in claim 4 including fastening the at least one core to the lumen with a fastener in order to fix the intraluminal device in the lumen.

6. The method of fixation of an intraluminal device as claimed in claim 5 wherein the fastener comprises a suture and the fastening includes applying the suture to the lumen.

7. The method of fixation of an intraluminal device as claimed in claim 6 including applying the suture around the at least one core when applying the suture to the lumen.

8. The method of fixation of an intraluminal device as claimed in claim 7 including wrapping a portion of lumen tissue around the at least one core when applying the suture around the core.

9. The method of fixation of an intraluminal device as claimed in claim 5 wherein the fastener comprises a clip.

10. The method of fixation of an intraluminal device as claimed in claim 5 including applying the fastener intraluminally.

11. The method of fixation of an intraluminal device as claimed in claim 5 including applying the fastener at an upstream end portion of said at least one core.

12. The method of fixation of an intraluminal device as claimed in claim 4 wherein said at least one core is removably connected with the portion of said wall with a removable attachment and including separating said at least one core by removing said removable attachment.

13. The method of fixation of an intraluminal device as claimed in claim 12 wherein said removable attachment comprises a severable filament.

14. The method of fixation of an intraluminal device as claimed in claim 13 including an enlarged member on said severable filament to space said severable filament from said wall for access to said filament.

15. The method of fixation of an intraluminal device as claimed in claim 4 wherein said at least one core is coated with a bio-compatible material that extends around the at least one core.

16. The method of fixation of an intraluminal device as claimed in claim 4 wherein said wall is used as an esophageal stent, an anti-reflux device, a nasal gastric tube, an intestinal sleeve, a bariatric device, or a metabolic disease treatment device.

17. The method of fixation of an intraluminal device as claimed in claim 4 including disrupting the tissue of the lumen where the at least one core is positioned against the lumen.

18. The method of fixation of an intraluminal devices as claimed in claim 17 including disrupting the tissue using at least one chosen from cauterization, ultrasound therapy, and cryo-therapy.

* * * * *